US011790171B2

(12) United States Patent (10) Patent No.: US 11,790,171 B2
Vianu et al. (45) Date of Patent: Oct. 17, 2023

(54) COMPUTER-IMPLEMENTED NATURAL LANGUAGE UNDERSTANDING OF MEDICAL REPORTS

(71) Applicant: Covera Health, New York, NY (US)

(72) Inventors: Ron Vianu, New York, NY (US); W. Nathaniel Brown, New York, NY (US); Gregory Allen Dubbin, New York, NY (US); Daniel Robert Elgort, New York, NY (US); Benjamin L. Odry, West New York, NJ (US); Benjamin Sellman Suutari, New York, NY (US); Jefferson Chen, New York, NY (US)

(73) Assignee: Covera Health, New York, NY (US)

( * ) Notice: Subject to any disclaimer, the term of this patent is extended or adjusted under 35 U.S.C. 154(b) by 818 days.

(21) Appl. No.: 16/849,506

(22) Filed: Apr. 15, 2020

(65) Prior Publication Data

US 2020/0334416 A1 Oct. 22, 2020

Related U.S. Application Data

(63) Continuation-in-part of application No. 16/386,006, filed on Apr. 16, 2019, now Pat. No. 11,521,716.

(51) Int. Cl.
*G06F 40/295* (2020.01)
*G16H 15/00* (2018.01)
(Continued)

(52) U.S. Cl.
CPC ............ *G06F 40/295* (2020.01); *G06F 40/10* (2020.01); *G06V 10/764* (2022.01); *G06V 10/82* (2022.01);
(Continued)

(58) Field of Classification Search
None
See application file for complete search history.

(56) References Cited

U.S. PATENT DOCUMENTS 10,839,164 B1 * 11/2020 Shorter .................. G06F 40/42
11,024,406 B2 * 6/2021 Sadeghi ................ G06Q 10/10
(Continued)

OTHER PUBLICATIONS

Gorinski, Philip John, et al. "Named entity recognition for electronic health records: a comparison of rule-based and machine learning approaches." arXiv preprint arXiv:1903.03985 (2019). (Year: 2019).*

(Continued)

*Primary Examiner* — Douglas Godbold
(74) *Attorney, Agent, or Firm* — Polsinelli, P.C.

(57) ABSTRACT

A natural language understanding method begins with a radiological report text containing clinical findings. Errors in the text are corrected by analyzing character-level optical transformation costs weighted by a frequency analysis over a corpus corresponding to the report text. For each word within the report text, a word embedding is obtained, character-level embeddings are determined, and the word and character-level embeddings are concatenated to a neural network which generates a plurality of NER tagged spans for the report text. A set of linked relationships are calculated for the NER tagged spans by generating masked text sequences based on the report text and determined pairs of potentially linked NER spans. A dense adjacency matrix is calculated based on attention weights obtained from providing the one or more masked text sequences to a Transformer deep learning network, and graph convolutions are then performed over the calculated dense adjacency matrix.

20 Claims, 6 Drawing Sheets

(51) Int. Cl.
*G06V 30/40* (2022.01)
*G06F 40/10* (2020.01)
*G06V 10/82* (2022.01)
*G06V 30/148* (2022.01)
*G06V 30/262* (2022.01)
*G06V 10/764* (2022.01)
*G06N 3/08* (2023.01)
*G06V 30/10* (2022.01)

(52) U.S. Cl.
CPC .......... *G06V 30/153* (2022.01); *G06V 30/262* (2022.01); *G06V 30/40* (2022.01); *G16H 15/00* (2018.01); *G06N 3/08* (2013.01); *G06V 30/10* (2022.01)

(56) References Cited

U.S. PATENT DOCUMENTS

| | | | | |
|---|---|---|---|---|
| 2013/0301920 | A1* | 11/2013 | Venkatapathy | G06F 40/58 382/182 |
| 2020/0065374 | A1* | 2/2020 | Gao | G06N 3/045 |
| 2020/0302117 | A1* | 9/2020 | Hu | G16H 30/40 |
| 2021/0183484 | A1* | 6/2021 | Shaib | G06F 40/295 |
| 2021/0286821 | A1* | 9/2021 | Liang | G06F 16/25 |
| 2022/0293253 | A1* | 9/2022 | Bunker | G06F 3/04842 |

OTHER PUBLICATIONS

Xu, Yan, Junichi Tsujii, and Eric I-Chao Chang. "Named entity recognition of follow-up and time information in 20 000 radiology reports." Journal of the American Medical Informatics Association 19.5 (2012): 792-799. (Year: 2012).*

International Preliminary Report on Patenabilit in related international application No. PCT/US2020/028288 dated Aug. 6, 2021.

Written Opinion of the International Preliminary Examining Authority in corresponding international application No. PCT/US2020/028288 dated Oct. 14, 2020.

International Search Report and Written Opinion in corresponding international application No. PCT/US2020/028288 dated Jun. 19, 2020.

"Recurent Neural Networks with Specialized Word Embeddings for Health-Domain Named-Entity Recognition", Journal of Biomedical Informatics, vol. 76, pp. 102-109, Dec. 1, 2017.

"Statistical Learning for OCR Error Correction", Information Processing and Management, vol. 54, No. 6, pp. 874-887, Nov. 1, 2018.

* cited by examiner

COMPUTER-IMPLEMENTED NATURAL LANGUAGE UNDERSTANDING OF MEDICAL REPORTS

CROSS-REFERENCE TO RELATED APPLICATIONS

This application claims the benefit of priority to U.S. patent application Ser. No. 16/386,006 filed Apr. 16, 2019 and entitled "COMPUTER-IMPLEMENTED DETECTION AND STATISTICAL ANALYSIS OF ERRORS BY HEALTHCARE PROVIDERS," the disclosure of which is herein incorporated by reference in its entirety.

TECHNICAL FIELD

The present disclosure relates generally to computer-implemented machine learning systems that are programmed to analyze digital image data alone or in combination with unstructured text, and more specifically pertains to methods for natural language understanding of radiology reports.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section. Further, it should not be assumed that any of the approaches described in this section are well-understood, routine, or conventional merely by virtue of their inclusion in this section.

In present healthcare practices, digital images and written reports, the latter typically from dictation, often serve as a basis of diagnostic assessment. Radiology is one example of a field in which images of patient anatomy, and dictated records of assessment by radiologists, often serve as core records reflecting a diagnosis. However, the interpretation of digital images is often complex, requiring significant medical and anatomical knowledge as well as an ability to detect subtle or complicated patterns of information in the correct context, and therefore the radiology field has a non-zero error rate, in which patients have had their diagnostic image data interpreted incorrectly, leading to the wrong diagnosis. The result can have a significant impact on patient comfort, care patterns, treatment outcomes and costs. For example, an erroneous diagnosis could lead to preparation for or performance of a surgical procedure that is unnecessary.

Some diagnostic errors result from deficiencies in a radiologist's skill in interpreting image data, other diagnostic errors result from differences in the communication of diagnostic information in written or dictated diagnostic reports. It is commonplace for different radiology practitioners to express a diagnosis in multiple different ways in writing, or with arcane or incorrect terms; some of these variations will correctly express a patient's diagnosis and many will convey an erroneous or misleading diagnosis.

A wide variety of diagnostic errors and quality issues occur with varying prevalence rates in patient exams. Examples of categories of diagnostic errors include: (1) false positive reporting of a diagnostic finding, (2) false negative reporting of a diagnostic finding, (3) errors in which a finding is "overcalled" or graded as being overly severe, or (4) errors in which a finding is "undercalled" or graded as being too minor. Other quality issues, related to communication issues in the report, can include the following categories: (1) findings that are reported in an overly equivocal manner, (2) findings that are reported in an overly vague manner, (3) findings that are reported with inappropriate emphasis, (4) inappropriate or lack of comparisons with prior diagnostic studies, (5) inappropriate or lack of inclusion of relevant standard measures (e.g. not using the Breast Imaging Reporting and Data System or BI-RADS scoring system for mammogram reports), or (6) inappropriate or lack of follow-up recommendations. Finally, diagnostic radiology exams can also suffer from technical errors and quality issues that can include: (1) poor image quality (e.g. low signal-to-noise ratio), (2) images degraded or obscured by patient motion or other artifacts, (3) poorly configured exam protocols (e.g. an MRI exam conducted without collecting images that have a necessary image contrast setting or images collected with resolution that is too low), or (4) poor anatomical coverage of the images.

Assessing the accuracy of diagnoses and presence of specific types of errors is difficult for patients and other stakeholders, including other physicians involved in a patient's care and healthcare payers. Presently, most efforts to assess the accuracy of a diagnosis rely on obtaining a second opinion from another radiologist or medical professional and then comparing the second opinion with the first opinion. While a diagnostic accuracy assessment could be based upon favoring the second opinion of an authoritative expert, the healthcare system might not be well-served if correct diagnoses only can be achieved by a subset of experts. Furthermore, authoritative experts are themselves fallible and pathological assessment always involves a measure of subjectivity, so it may be difficult to determine if variation across the two diagnoses represent evidence of diagnostic errors present in at least one diagnosis or if the variation represents multiple ways of stating the same diagnosis. Seeking a third or multiple additional opinions on a given patient's diagnosis does not alleviate this issue and is likely prohibitive due to logistics or cost for most patients.

Therefore, there is a long-felt need in the field for a standardized, robust, and quantitative method for assessing the accuracy of patients' diagnoses and the diagnostic accuracy and error rates achieved by radiology providers. However, this requires a scalable system for standardizing multiple aspects of the diagnostic quality assessment process, including, (1) the diagnostic interpretation of image data, (2) the documentation of diagnostic findings in dictated or written diagnostic reports, and (3) the categorization of various diagnostic errors and quality issues.

While extensive medical records are usually developed for each patient in digital electronic form, typically much of the data is unstructured; examples are the digital medical images and dictated diagnostic reports, both of which are non-standardized across patient exams and not readily interpretable by machines or computers. While more structured dictation could be provided, it is an imperfect approach that is unlikely to be adopted on a widespread basis. Additional tools or systems are required to transform the unstructured information in medical images and diagnostic reports into standardized data that can be leveraged for assessment of diagnostic accuracy, error rates, and quality.

Since a multitude of diagnostic errors and related quality issues are possible in the context of most diagnostic imaging exams, it can be valuable to prioritize the specific types of diagnostic findings and diagnostic errors that a diagnostic accuracy and quality assessment system will target for evaluation. One approach to prioritization is to identify general aspects of diagnoses that are clinically meaningful for patients' care patterns and/or outcomes and achieve high degrees of agreement between radiologist. Since perfect agreement between radiologists is not likely in any category of diagnostic finding or diagnostic error, and the levels of agreement exhibit a wide variability across categories of diagnostic findings and errors, is can be valuable for a diagnostic accuracy and quality assessment system to be able to appropriately quantify the amount of agreement that radiologists exhibit in each category of diagnostic finding and error under evaluation.

Key outputs from diagnostic accuracy and quality assessment systems include estimates of the accuracy rates and error rates that are achieved by a radiology provider under evaluation. However, if estimates of accuracy rates and error rates are directly based on data generated by independent radiologists who use a standardized process for identifying and characterizing selected diagnostic findings and diagnostic errors, the estimates will themselves not be accurate or reliable due to inter-radiologist variability.

Stakeholders in the healthcare ecosystem have developed an increased interest in quantitative and reliable healthcare quality metrics that are highly correlated with patient outcomes, patient comfort or quality of life, and costs. However, since not all diagnostic errors and quality issues have the same impact on downstream patient care patterns or patient outcomes, straightforward estimates of diagnostic accuracy rates or error rates may not represent a valuable quality metric.

When using a diagnostic accuracy and quality assessment system to evaluate multiple distinct providers, it is critical to account for the fact that different providers often care for very different patient populations. It may be inappropriate to use unadjusted estimates of diagnostic accuracy rates or error rates as standardized and generalizable measures of radiology care quality. A quality assessment system that can be used across a diverse population of providers will usually need to include some adjustment for differences between the relevant patient populations.

Furthermore, there is an acute need for computer-implemented techniques that can generate data representing the quality or accuracy of medical diagnoses in a robust and scalable manner. In some instances, institutions have attempted to replace or supplement radiologists, in the context of their clinical workflow as they perform initial interpretations of image data and generate diagnostic reports, with machine-executed image recognition and interpretation systems. These systems are programmed to inspect images and flag abnormalities. However, known systems typically identify too many false positives, or work only with abnormalities that are straightforward to find in an image, and therefore they do not add significant value to the ecosystem in this capacity.

Computer-implemented image interpretation and medical report interpretation technologies have not been developed, expanded, or adapted for use as part of a diagnostic accuracy and quality assessment system. The technical performance and design requirements for these technologies are different in this distinct application domain. In the context of an initial interpretation of image data to support (or replace) a radiologist as they generate a specific patient's diagnostic report, a computer-implemented image interpretation system will need to achieve high sensitivity, high specificity, and an ability to target a wide range of diagnostic finding types. In the context of a diagnostic accuracy and quality assessment system that is supplemented with or solely executed by a computer-implemented image interpretation system, which will also need to be integrated with a computer-implemented medical report interpretation system, there are more relaxed performance requirements with respect to sensitivity, specificity, and variety of targeted diagnostic finding types. The reason for this relaxation of performance requirements is that, as long as the sensitivity and specificity performance levels of the computer implanted systems is quantified, it is still possible calculate robust and reliable estimates of the overall diagnostic accuracy and error rates, along with appropriate confidence intervals around these estimates, that radiology providers achieve when caring for populations of patients.

SUMMARY OF THE INVENTION

According to an aspect of the present disclosure, provided are systems and methods for natural language understanding. A natural language understanding method begins by obtaining a radiological report text, the radiological report text containing one or more clinical findings. In response to detecting one or more errors in the radiological report text, a best replacement candidate for each of the one or more errors is substituted, the best replacement candidate calculated by analyzing a plurality of character-level optical transformation costs weighted by a frequency analysis over a corpus corresponding to the radiological report text. For each given word within the radiological report text, the method further comprises: obtaining a word embedding; determining a plurality of character-level embeddings; and concatenating the word embedding and the plurality of character-level embeddings to a neural network. Using the neural network, a plurality of NER tagged spans are generated for the radiological report text, the generating based on the concatenated word and character-level embeddings. The method further comprises calculating a set of linked relationships for the plurality of NER tagged spans by: generating one or more masked text sequences based on the radiological report text and determined pairs of potentially linked NER spans; calculating a dense adjacency matrix based on attention weights obtained from providing the one or more masked text sequences to a Transformer deep learning network; and performing graph convolutions over the calculated dense adjacency matrix via a graph convolutional network.

In an aspect of the disclosure, using the neural network to generate the plurality of NER tagged spans comprises: classifying each given word within the radiological report text by applying an IOB (Inside-Outside-Beginning) tagging scheme; generating a plurality of spans from words having a Beginning tag or an Inside tag; and generating the plurality of NER tagged spans by classifying each one of the plurality of spans over a pre-defined set of classes.

In a further aspect of the disclosure, the pre-defined set of classes comprises a Pathology class, a Severity class, and a Location class.

In a further aspect of the disclosure, the method further comprises training a classifier over a pre-defined lexicon of clinical terminology; and providing the plurality of NER tagged spans to the trained classifier, such that the trained classifier labels NER tagged spans of the Pathology class with a specific pathology type In a further aspect of the disclosure, the method further comprises providing the plurality of NER tagged spans to the trained classifier such that the trained classifier: labels NER tagged spans of the Severity class with a severity level; and labels NER tagged spans of the Location class with a specific anatomical location.

In a further aspect of the disclosure, the severity level is a continuous numerical score value; and the anatomical location is a specific motion segment.

In a further aspect of the disclosure, the pre-defined lexicon of clinical terminology comprises a pre-trained model of biomedical word embeddings or Word2vec encodings.

In a further aspect of the disclosure, the neural network used to generate the plurality of NER tagged spans is an ordered-neuron Long short-term memory (ON-LSTM) using a conditional random field (CRF) to classifying the plurality of spans over the pre-defined set of classes.

In a further aspect of the disclosure, obtaining the radiological report text comprises providing an image of a radiological report to one or more optical character recognition (OCR) engines, the radiological report text generated from the outputs of the one or more OCR engines.

In a further aspect of the disclosure, the plurality of character-level optical transformation costs is used to calculate weighted Levenshtein distances between a detected error word in the radiological report text and a plurality of potential replacement candidate words.

In a further aspect of the disclosure, the corpus corresponding to the radiological report text is a corpus of terms specific to a determined type of radiological exam represented in the radiological report text.

In a further aspect of the disclosure, the method further comprises in response to detecting one or more errors in the radiological report text: generating a plurality of potential replacement candidates based on the analysis of the character-level optical transformation costs and the frequency analysis; obtaining embeddings for one or more words adjacent to the detected error in the radiological report text; analyzing each potential replacement candidate against the embeddings of the one or more adjacent words, using a masked language model; and calculating the best replacement candidate based on the highest probability output from the masked language model analysis.

In a further aspect of the disclosure, the masked language model is Clinical BERT-based (Bidirectional Encoder Representations from Transformers) machine learning network.

In a further aspect of the disclosure, the method further comprises using the masked language model to calculate a clinical significance of mistake for each potential replacement candidate by analyzing each potential replacement candidate against the embeddings of the one or more adjacent words.

In a further aspect of the disclosure, generating the one or more masked text sequences comprises, for each given pair of potentially linked NER tagged spans: obtaining, from the radiological report text, a sentence portion containing both NER tagged spans of the given pair; masking both NER tagged spans with an identifier, the identifier corresponding to a class of the NER tagged span; and generating a masked text sequence for the given pair by replacing the NER tagged spans in the sentence portion with the identifiers.

In a further aspect of the disclosure, generating the one or more masked text sequences comprises generating a single masked text sequence for the plurality of potentially linked NER tagged spans by: masking each NER tagged span of the plurality of potentially linked NER tagged spans with an identifier, the identifier corresponding to a class of the NER tagged span; and generating the single masked text sequence by replacing each NER tagged span in the radiological report text with its corresponding identifier.

In a further aspect of the disclosure, the method further comprises providing the single masked text sequence to a BERT-AL (BERT for Arbitrarily Long Document Understanding) machine learning network.

In a further aspect of the disclosure, the method further comprises calculating the set of linked relationships for the plurality of NER tagged spans by providing to a dense classifier the output of the graph convolutions over the calculated dense adjacency matrix, and one or more head masks and tail masks calculated for the masked text sequences provided to the Transformed deep learning network.

In a further aspect of the disclosure, training the classifier over a pre-defined lexicon of clinical terminology further comprises refining the classifier by generating augmented training data, the augmented training data generated in response to analyzing a first pass classification performed using the pre-defined lexicon of clinical terminology.

In a further aspect of the disclosure, the method further comprises iteratively generating augmented training data based on an analysis of a prior training round to detect words having a low frequency of occurrence and a high feature weight in a classification model of the classifier.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
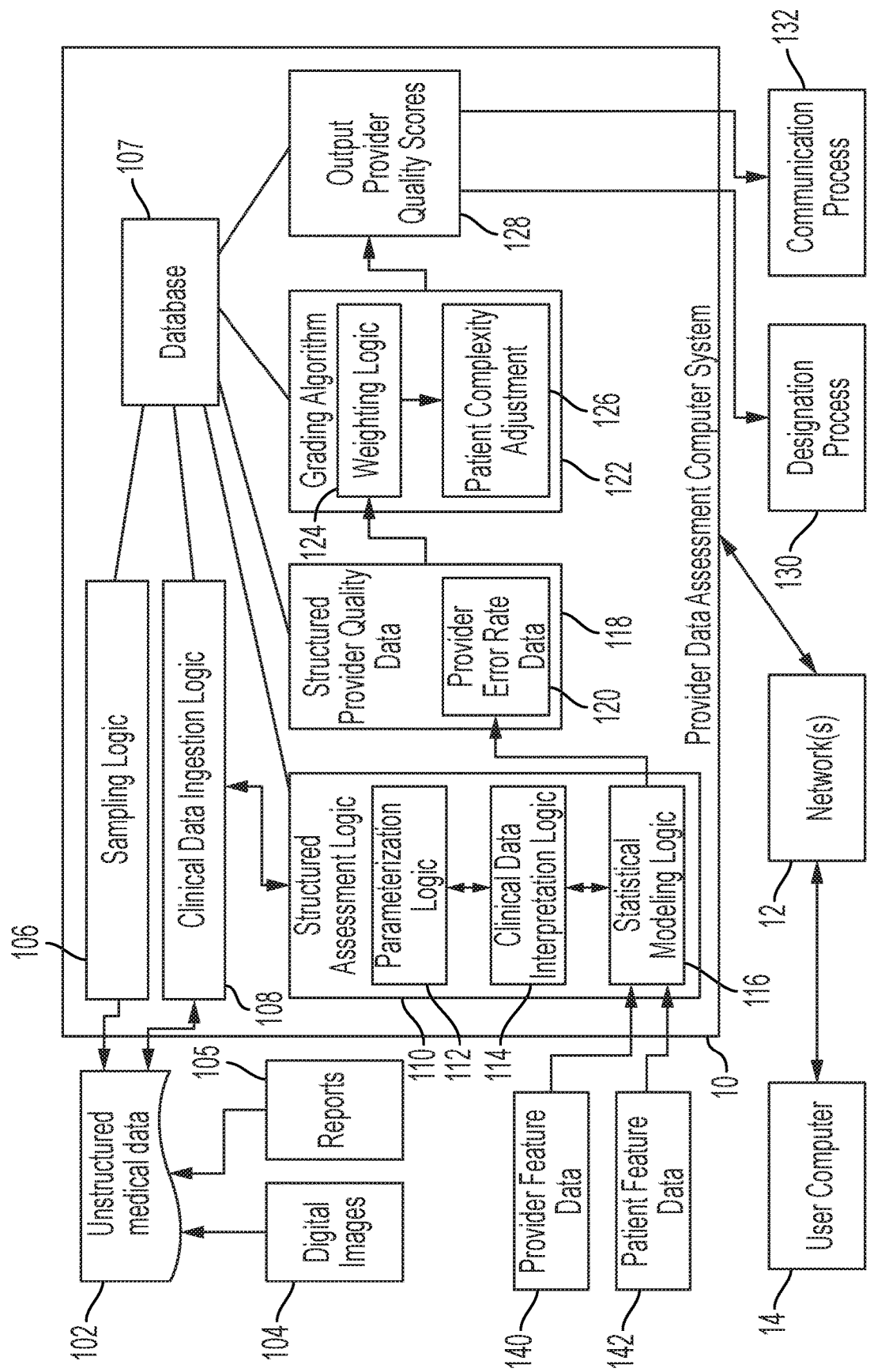
FIG. 1 illustrates an example of functional elements and data flows in a distributed computer system that may be used to implement one embodiment of provider assessment processing.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Additional features and advantages of the disclosure will be set forth in the description which follows, and in part will be obvious from the description, or can be learned by practice of the herein disclosed principles. It will be appreciated that for simplicity and clarity of illustration, where appropriate, reference numerals have been repeated among the different figures to indicate corresponding or analogous elements. The description is not to be considered as limiting the scope of the embodiments described herein.

Using various machine learning techniques and frameworks, it is possible to analyze data sets to extract patterns and correlations that may otherwise have not been apparent when subject to human analysis alone. Using carefully tailored training data inputs, a machine learning system can be manipulated to learn a desired operation, function, or pattern. The performance of a machine learning system largely depends on both the quality and the quantity of these carefully tailored data inputs, also known as training data. Machine learning is capable of analyzing tremendously large data sets at a scale that continues to increase; however, the ability to build and otherwise curate appropriately large training data sets has lagged and continues to be a major bottleneck in implementing flexible or real-time machine learning systems.

A detailed description of example methods for natural language understanding pipelines and/or natural language processing (NLP) pipelines that may be applied to input radiological report text as referenced above, is provided below in Sections 7 and 8. Section 7 provides a general overview and Section 8 provides architecture details.

1. General Overview

In an embodiment, a system for quantifying diagnostic radiology errors uses structured and standardized exam reviews that are performed by independent radiologists to create a repository of clinically meaningful attributes of radiology images and radiology reports. Digital analysis of the attributes yields an objective truth source for any diagnosis that can be associated with digital images of anatomy or other physical features of the subject as well as an objective truth source for any diagnostic error or quality issue associated with the manner in which diagnoses were described or omitted from the radiology report.

A modified embodiment may supplement the attributes, or categories of attributes, with reliable measures of confidence or probability of correctness. These reliable measures of confidence or probability of correctness may be generated by statistical analysis of the variances across the attributes in reports that were generated by the radiologists performing structured and standardized radiology exam reviews. In some cases, the radiologists performing structured and standardized radiology exam reviews will independently review the same underlying radiology exam and generate reports that will contribute to the analysis of variance.

The techniques herein are most suitable for assessing diagnostic accuracy, errors, and/or quality related to pathology or disease that is subject to generally good agreement among experts with respect to physical features that are present, location, size and so forth.

In some embodiments, the system for quantifying diagnostic radiology errors will be optimized to generate accurate quantitative measures of diagnostic error rates and quality issues related to specific radiology providers that are selected for assessment and their associated performance with respect to specific pathologies and diseases. These quantitative measures of diagnostic error rates may be aggregated to varying levels of anatomical detail, for example: (1) a combined measure representing the rate of any error that a radiology provider makes in the context of diagnostic knee MRI exams, or (2) a more narrow-scope measure representing the rate of any error that a radiology provider makes pertaining to an accurate diagnosis of meniscal tears within knee MRI exams. These quantitative measures of diagnostic error rates may also be aggregated to varying levels of diagnostic error types, for example: (1) a measure representing the rate of any false positive errors that a radiology provider makes in the context of diagnostic imaging exams, or (2) a measure representing the rate of any errors in which a finding is "undercalled", or mistakenly graded as being too minor, that a radiology provider makes in the context of diagnostic imaging exams. Finally, these quantitative measures of diagnostic error rates may be aggregated to varying levels of within a radiology provider organization, for example: (1) a measure representing the rate of any diagnostic error that an individual radiologist makes in the context of selected diagnostic imaging exam types, or (2) a combined measure representing the rate of any error that a group of radiologists who practice together at single radiology facility make in the context of selected diagnostic imaging exam types.

In some embodiments, the measures of diagnostic error rates will be entirely based on the empirical diagnostic error data and attributes that are produced by the independent radiologists who perform standardized reviews of the exams performed by the radiology providers under review. In some embodiments, the measures of diagnostic error rates will be based, all or in part, on statistical modeling, including hierarchical Bayesian statistical modeling, of the empirical diagnostic error data and attributes.

Some embodiments of the system for quantifying diagnostic radiology errors will also be optimized to generate measures of diagnostic quality that are modified versions of radiology provider error rates. These measures of diagnostic quality may be weighted combinations of specific diagnostic errors, such that the weighting may represent the relative likelihood that a specific type of diagnostic error will have an impact on patients' treatment pathways, clinical outcomes, or costs of treatment and subsequent care. The method for combining the various diagnostic error rates into the new quality measure may involve weighted averaging, linear or non-linear statistical modeling, or machine learning. The assignment of weights that represent the likelihood that specific types of diagnostic errors will have a clinical impact on patients may be accomplished by: (1) capturing additional data elements during the standardized diagnostic exam reviews, (2) stand-alone assessments by radiologist or other medical experts of the likely clinical impact of specific types of diagnostic errors, or (3) analysis of historical medical records of patients in combination with diagnostic error data to estimate the correlation of specific diagnostic errors or providers with specific error rates and impacts to patients' treatment patterns, costs, and outcomes.

In some embodiments, the diagnostic error data and attributes that are generated through standardized review of imaging exams will be supplemented with additional data and attributes about the radiology providers under evaluation. Examples of these supplementary data and attributes may include: (1) radiologists' educational history, including fellowship training status, (2) radiologists' years of practice, (3) radiologists' historical exam volume and case mix, (4) radiology facilities' imaging equipment, or (5) radiology facilities' imaging exam protocol configurations. This supplementary data and attributes may be leveraged by the system to: (1) generate measures of diagnostic error rates or weighted diagnostic error rates with improved accuracy, precision, or narrower confidence intervals; or (2) to generate predicted measures of diagnostic error rates or weighted diagnostic error rates for radiology providers which have not had any of their imaging exams subjected to standardized reviews and for whom only the supplementary data elements and attributes are available. The methodologies that can be employed to leverage the supplementary radiology provider data and attributes in this way involves modeling the correlations between these new supplementary data elements and the data elements related to diagnostic errors and quality issues that are generated by the standardized imaging exam reviews; the quantitative methodologies that are used in this context may include Bayesian or log-linear statistical modeling or machine learning techniques.

In some embodiments the system for quantifying diagnostic radiology errors will also be optimized to generate measures of diagnostic quality that are also adjusted for patient complexity, such that radiology providers may be penalized less for having higher rates of diagnostic errors when caring for a population of more complex patients and vice versa. To quantify the complexity of individual patients and populations of patients that are associated with the various radiology providers under evaluation, the system may leverage combination of data from: standardized reviews of imaging exams, billing or claims data, patient demographic data, or other data extracted from electronic medical records. The system may employ Bayesian or log-linear statistical modeling, linear or non-linear regression, or machine learning methodologies to achieve the patient complexity adjustment of the diagnostic quality measures.

In one embodiment, patient complexity is adjusted for using a two-step process. In step one, diagnostic error rate estimates for each radiology provider under evaluation are modeled as conditional probabilities, i.e. diagnostic errors rate for each provider are estimated conditional on the presence of specific medical conditions and severities across the patient population observed for the radiology provider. We denote the computed estimates (e.g., via regression) of these conditional probabilities as $P_r(Y|P=p)$, where Y is a variable representing diagnostic error rate and $P=p$ is a specific medical condition and severity; and we further denote the distribution of all medical conditions and severities observed for the radiology provider as $f(P=p)$, at each level of which we have the aforementioned estimated conditional probability.

In step two, a data set is defined that represents a reference patient population $f(P^*=p^*)$, which has a fixed distribution of medical conditions and severities (this distribution can be modeled using empirical observations or a reference patient population can be created with an arbitrary distribution of medical conditions and severities for this purpose). The diagnostic error rates estimated for each radiology provider, as conditional probabilities from step 1, can then be evaluated with respect to this distribution, i.e., $E[f(Y'|P=p=p^*)|f(P^*=p^*)]$ can be calculated for different providers, and these results can be directly compared to evaluate relative provider performance with respect to the same reference patient population. This two-step process allows an "apples to apples" comparison of diagnostic error rates across radiology providers that is not confounded by differences in the complexity of the patient population the radiology providers happen to be observed treating. In some embodiments the attributes generated by the standardized exam reviews are used to train computer-implemented machine learning algorithms, for example recurrent neural networks or deep learning algorithms, such that the computer-implemented algorithms can then independently analyze digital radiology images and radiology reports and automatically apply the attributes that are included in the standardized exam reviews. These computer-implemented and algorithms will be trained to analyze radiology images to identify the presence or absence and severity of the specific pathologies that are assessed by the radiologists when they perform the standardized exam reviews. When analyzing the images, the algorithms may also be trained to generate attributes that describe the technical quality of the images, for example: (1) poor image quality (e.g. low signal-to-noise ratio), (2) images degraded or obscured by patient motion or other artifacts, (3) poorly configured exam protocols (e.g. an MRI exam conducted without collecting images that have a necessary image contrast setting or images collected with resolution that is too low), or (4) poor anatomical coverage of the images. The computer-implemented and algorithms will also be trained to analyze radiology reports to identify the presence or absence of specific diagnostic findings in the reports as well as the severity of the pathologies that are reported. For example, aspects of such capabilities are subsequently described in greater depth in Sections 7 and 8, directed to a natural language understanding pipeline. When analyzing the radiology reports, the algorithms may also be trained to generate additional attributes related to the quality of the report, for example: (1) findings that are reported in an overly equivocal manner, (2) findings that are reported in an overly vague manner, (3) findings that are reported with inappropriate emphasis, (4) inappropriate or lack of comparisons with prior diagnostic studies, (5) inappropriate or lack of inclusion of relevant standard measures (e.g. not using the Breast Imaging Reporting and Data System or BI-RADS scoring system for mammogram reports), or (6) inappropriate or lack of follow-up recommendations. Once the algorithm performs its assessment on the images and report associated with a specific patient exam, it will compare its assessment of the pathologies in the images with its assessment of the diagnostic findings present in the radiology report to create attributes that represent the accuracy of the radiology report and any diagnostic errors that exist.

In some embodiments, the computer-implemented algorithm will produce measures of uncertainty for each attribute it generates related to the radiology images, radiology reports, and diagnostic errors. These measures of uncertainty will be based on quantitative assessments of the computer-implemented algorithm's performance in training and validation datasets. The measures of uncertainty may also incorporate measures of the underlying variability in accuracy of the training and validation datasets themselves.

The same statistical modeling methodologies described above may be applied to the diagnostic error attributes generated by the computer-implemented algorithms, in order to calculate estimates of radiology provider diagnostic error rates and weighted measures of diagnostic error rates and diagnostic accuracy. As described above, some embodiments may supplement the diagnostic error attributes with additional attributes related to radiology provider characteristics in order to generate measures of diagnostic error rates or weighted diagnostic error rates with improved accuracy, precision, or narrower confidence intervals The analytic approaches of embodiments may execute as overnight or background processes at any time after physicians or practitioners generate new radiology images or submit new radiology reports. In some embodiments, the processes described for FIG. 1, FIG. 3 may be executed in real-time immediately after a physician submits a report to provide immediate feedback to the healthcare provider in the form of a quality review or quality report. Or, data indicating errors can be communicated to an administrator, third-party reviewer, or other system or program without direct notification to the primary physician who submitted a report. Or, in yet another alternative, errors may be scored and ranked according to seriousness or severity, and only errors above a threshold severity value may be communicated to the primary physician.

For purposes of illustrating clear examples, certain aspects of this disclosure expressly refer to use in the context of radiology practice. However, the principles of this disclosure and other embodiments may be used in connection with any other kind of healthcare practice and embodiments are not limited to radiology. Furthermore, for purposes of this disclosure, certain embodiments are described using terms having the following definitions:

Location—a region of the human body admitting specific distinct, though perhaps related, pathologies.

Pathology—a well-defined malady, for example, "central canal stenosis of the L2-3 segment in the lumbar spine".

Item—a checklist question engineered to elicit a pathology-specific diagnosis.

Diagnosis—a selected value for an item, such as None, Small, Medium, Large.

Checklist—a collection of items capturing a specific diagnosis for a particular medical discipline or specialty.

Reading provider—a physician or practitioner who is the one providing diagnoses for evaluation.

Reviewing provider—a physician or practitioner who is evaluating the diagnoses of a reading provider after the fact, for accuracy.

Practice—a group of providers that is defined by business or geographic attributes.

Provider—a broad term for a physician, other healthcare practitioner, practice, group or other aggregation.

2. Overview of Example Diagnostic Quality Assessment Framework for Radiology

FIG. 1 illustrates an example of functional elements and data flows in a distributed computer system that may be used to implement one embodiment of provider assessment processing. In an embodiment, computer-implemented processes may be programmed to support assessment of the quality level of radiology providers and practices. Other embodiments may be applied to other medical disciplines.

In one embodiment, a provider data assessment computer system 10 comprises sampling logic 106 which receives unstructured medical data 102 as input, clinical data ingestion logic 108 and structured assessment logic 110 which may receive provider feature data and patient feature data for use in executing statistical modeling operations as further described herein. These functional elements cooperate, under program control as further described functionally herein, to generate structured provider quality data 118, which may be provided as input to a grading algorithm 122 for calculation of output provider quality scores 126. The resulting scores may be provided to or used as part of a designation process 130 and/or communication process 132. A digital database 107 may be programmed to store the unstructured medical data 102 after input as well as the structured provider quality data 118, output provider quality scores 126, feature data 140, 142, and other data such as pathology prevalence data and error data for different fields of specialty.

Computer system 10 may be implemented using one or more distributed or networked computers, services, processes or other software elements hosted using desktop computers, on-premises server computers or cloud computing instances of virtual computing centers. Each of the functional elements of computer system 10 may execute as a separate asynchronous thread, service or method. In some embodiments, multiple instances of functional elements may be provided. For example, structured assessment logic 110 may execute as a plurality of independent instances in a virtualized computer to enable parallel processing of multiple datasets or parts of a single dataset. In some embodiments, aspects of structured assessment logic 110 may be programmed as a SaaS application hosted on a web server to communicate with a browser executed at a user computer 14 that is coupled to computer system 10 directly or indirectly via one or more computer networks 12 or internetworks.

One practical application of computer system 10 is detection and measurement of observed diagnostic error rates for sampling of clinical exams from radiology providers. In an embodiment, sampling logic 106 is programmed to identify which types of exams and how many clinical exams to sample from radiology providers. Exams may be represented in digital images 104, typically associated with reports 105 consisting of digitally stored text, as part of unstructured medical data 102. For example, a particular report among the reports 105 may represent a set of comments or notes on pathological structures that are visible or believed to be visible in one or more associated digital images 104. Thus, reports 105 typically represent physicians' diagnostic findings with respect to corresponding specific digital images 104, and there may be thousands or millions of sets of images and reports for different patients, exams and diagnoses. In some embodiments, sampling logic 106 is programmed to calculate a sample of exams based upon an estimated or measured prevalence of key pathologies and diagnostic errors, combined with specific criteria relating to a particular kind of designation of the provider.

For example, if the unstructured medical data 102 consists of scans of lungs, and data in database 107 indicates that lung scans have a low prevalence of lung cancer pathology as well as a low percentage of diagnostic errors for lung cancer, then the sampling logic 106 may apply a programmed rule to select a relatively high percentage, for example 50%, of all the exams for further analysis. In contrast, a different set of scans with higher pathology prevalence and/or a higher known percentage of diagnostic error might trigger a programmed rule of the sampling logic 106 to select a lower percentage, for example 10%, of all exams in the set for analysis. Furthermore, the resulting percentage or number of exams that are selected by the sampling logic 106 may be weighted or biased by other attributes and data elements in database 107 related to the provider that provided the unstructured medical data 102, for example: pre-existing quality designations or error rate estimates, the provider's patient volumes or cases mixes, or fellowship training status of providers.

In an embodiment, clinical data ingestion logic 108 is programmed to capture raw clinical data. For radiology providers, raw clinical data may comprise medical images, which could be in the form of DICOM files, and diagnostic reports, as represented by digital images 104 and reports 105. Or, digital images 104 may comprise any form of graphical images that are captured in a radiology practice including X-ray, MRI or CT images, digital film or other diagnostic data. Images 104 may be associated with corresponding reports 105, which consist of text in any digitally stored form. As previously noted, embodiments are not limited to radiology and other disciplines may interoperate with the processes herein based on raw clinical data of other types. For other providers, the type of raw clinical data may comprise electronic medical record (EMR) records or files, free-text notes, PDF files scanned from notes or generated from text files such as dictations, non-digital data such as the contents of a paper chart that has been scanned into image form or processed using optical character recognition (OCR), image-based diagnostic tests other than radiology imagery, claims data, billing data, employer-specific work data, audio files such as recordings of consultations or office visits with physicians or transcripts of the audio files, video recordings of surgeries or other interventions or procedures, or data from wearable devices. In some instances, raw clinical data may be partly structured; for example, data files may include metadata such as provider credentials, equipment attributes, length of exam, demographic or diagnostic features of patients.

It will be apparent that with datasets of the foregoing type, determining whether diagnostic errors have occurred, or other aspects of the quality of a diagnosis, cannot be obtained directly from the data. Quality attributes may relate to the technical performance of a diagnostic exam, such as poor-quality images or images that do not sufficiently cover the necessary anatomy. In an embodiment, elements of FIG. 1 are programmed to transform the unstructured raw clinical data described above into at least partly structured data, and structured review procedures and machine-executed statistical analysis are performed to analyze the available data to derive error data and quality score values. Consequently, useful and meaningful values are extracted from previously non-usable data.

In an embodiment, clinical data ingestion logic 108 is programmed to use OCR and natural language processing (NLP) techniques, which may be implemented in external code libraries or web services, to convert unstructured diagnostic report text to structured, machine-readable data. In an embodiment, clinical data ingestion logic 108 is programmed to use image processing libraries or functions to convert medical image data into structured, machine-readable data. For example, clinical data ingestion logic 108 may be programmed to perform image feature identification in digital images 104 and generate output data comprising a graph, tree or list of features that have been identified.

Other functional elements of computer system 10 are programmed to determine what diagnostic errors were made. In radiology, for example, errors could arise from low-quality images, motion artifacts from movement of the patient at the time of capturing an image, poor positioning of anatomy in relation to a camera or scanner, and so forth. In an embodiment, trained primary physicians initially prepare the raw clinical data and images, and secondary reviewers use structured processes to assess features for quality.

In an embodiment, structured assessment logic 110 is programmed with parameterization logic 112 to execute clinical data assessment parameterization. The parameterization logic 112 executes in the context of a set of one or more digital images, from among the digital images 104, that have been reviewed by a primary physician or practitioner and interpreted in a corresponding report from among the reports 105. Thus, a particular report 105 comprises a written interpretation of a set of associated images, completed by a primary physician. The parameterization logic 112 may be programmed to:

A. Select a set of one or more digital images from among the digital images 104 and a corresponding report 105, automatically according to a workflow or order, or based on input from user computer 14. The user computer 14, in this example, is associated with a secondary physician reviewer. In some embodiments, parameterization logic 112 may be programmed to present a list of available images in a graphical user interface with GUI widgets that are programmed to indicate selection of particular images.

B. Present the corresponding report via output to a computer display device of the user computer 14 and wait for user input to interpret the report.

C. Select a structured checklist, from among a plurality of structured checklists that are stored in database 107, that applies to the digital image, a medical field that is associated with the selected digital image, or that is specified in configuration data. Each checklist may be digitally stored in the database 107 as a row of a database table in which columns represent diagnostic dimensions or parameters, and then rendered in a graphical user interface in the form of a checklist under program control; thus, literal storage as a document is not required and digital data structures may be used to represent checklists in storage.

D. Render and display the structured checklist via output to a computer display device of the user computer 14 and wait for user input to respond to items in the checklist in reference to the current digital image. The secondary physician reviewer follows the checklist to detect and measure the prevalence of diagnostic errors and to control the generation of training data for artificial intelligence logic such as a neural network or classifier. The checklist addresses key diagnostic dimensions or parameters in interpretation of the digital images 104 for radiology or other specialties, customized to specific anatomical areas. Checklists may be created and stored in advance for any medical discipline and the key dimensions or parameters of quality of a checklist will reflect that discipline. For example, a checklist may prompt for input from user computer 14 to indicate (a) whether disc herniation is present in the L4-5 lumbar spine and (b) if present, whether it is small, moderate or large. Input from user computer 14 may be stored in database 107 in association with identifiers of a dataset, a particular digital image among the digital images 104, a checklist and a user account. Furthermore, for some disciplines, the use of a checklist with digital image data will not be required and checklists may be assessed based on written reports or text data, as next described.

In an embodiment, the secondary reviewer physician compares their interpretation of the digital images with the original physician's diagnostic report as abstracted by the checklist. The reviewer then uses the checklist and uses GUI widgets generated and displayed by the clinical data interpretation logic 114 to parameterize the level of agreement or disagreement between the reviewer's interpretation and the original interpretation, producing data that describes diagnostic errors. In some embodiments, clinical data interpretation logic 114 may be programmed to presume that the reviewer is correct, but some embodiments may model, under program control, variability of interpretation among reviewers, as further described.

E. Repeat the foregoing steps for all checklists applicable to the current digital image.

F. Return to the first step to process a different digital image or return control to the user computer or another system, program or process.

In this manner, computer-implemented processing may be used to cause database 107 to develop a comprehensive dataset that characterizes issues associated with a large number of digital images associated with exams. In some embodiments, each stored checklist later may be used as a portion of training data for training the statistical modeling logic 116 when implemented as a neural network or classifier. After a training phase, in an evaluation phase, the statistical modeling logic 116 may execute to receive the digital images 104, receive the reports 105, interpret the images according to one or more checklists, interpret the original physician's diagnostic report according to the checklist, compare the machine-generated interpretation of the images to the original physician's diagnostic report, utilizing the checklist to parameterize levels of agreement or disagreement, and generate output data identifying diagnostic errors with associated confidence level values. The statistical modeling logic 116 may receive provider feature data 140 and patient feature data as input to adjust the classification of images and reports, and output error data, based on variable features of providers and patients, as further described in other sections. Broadly, statistical modeling logic 116 executes as a trained classifier to detect errors in unstructured medical diagnostic data after training on similar medical diagnostic data in which errors have been explicitly identified.

One result of processing using the statistical modeling logic in this manner may be provider error date data 120, which may form one component of stored, structured provider quality data 118. In an embodiment, structured provider quality data 118 may be used in several different ways.

A. In an embodiment, the quality data 118 may be provided as input to the grading algorithm 122, which is programmed to use weighting logic 124 and patient complexity adjustment 126 to transform the error data.

In an embodiment, weighting logic 124 applies weight values to quality scores based on a combination of expert clinical input and data-drive insights about outcomes. These factors may be used to calculate weight values to assign to specific diagnostic errors, representing a weight of that error relative to its impact on later clinical care or treatment. Thus, a particular error may have a high weight value if its impact on clinical care or treatment, such as the complexity of a later treatment, patient discomfort or cost is high. Thus, a particular quality score 128 may be adjusted upward or downward based on the weight value associated with the error(s) represented in error rate data 120 that led to the score.

Patient complexity adjustment 126 is programmed to obtain data from database 107 for patient complexity including but not limited to demographic data such as age and sex, and clinical interpretation data such as number and severity of the pathologies identified in exams. Therefore, particular healthcare providers are not inappropriately credited or penalized, as part of determining quality scores 128, based on patient population dynamics. In this manner, grading algorithm 122 may be programmed to output provider quality scores 128, representing an overall quality score for a particular healthcare provider based on its error rate, the complexity of patients seen, and various features of the provider.

B. The quality scores 128 may be used in a designation process 130 to designate a particular healthcare provider using a particular label or designation from among a plurality of different labels or designations, using an ordered scale, hierarchical arrangement or other association of labels.

C. The quality scores 128 also may be provided to healthcare providers according to a structured communication process 132.

3. Overview of Estimating Diagnostic Error Rates Using Statistical Algorithms

Figure 2:
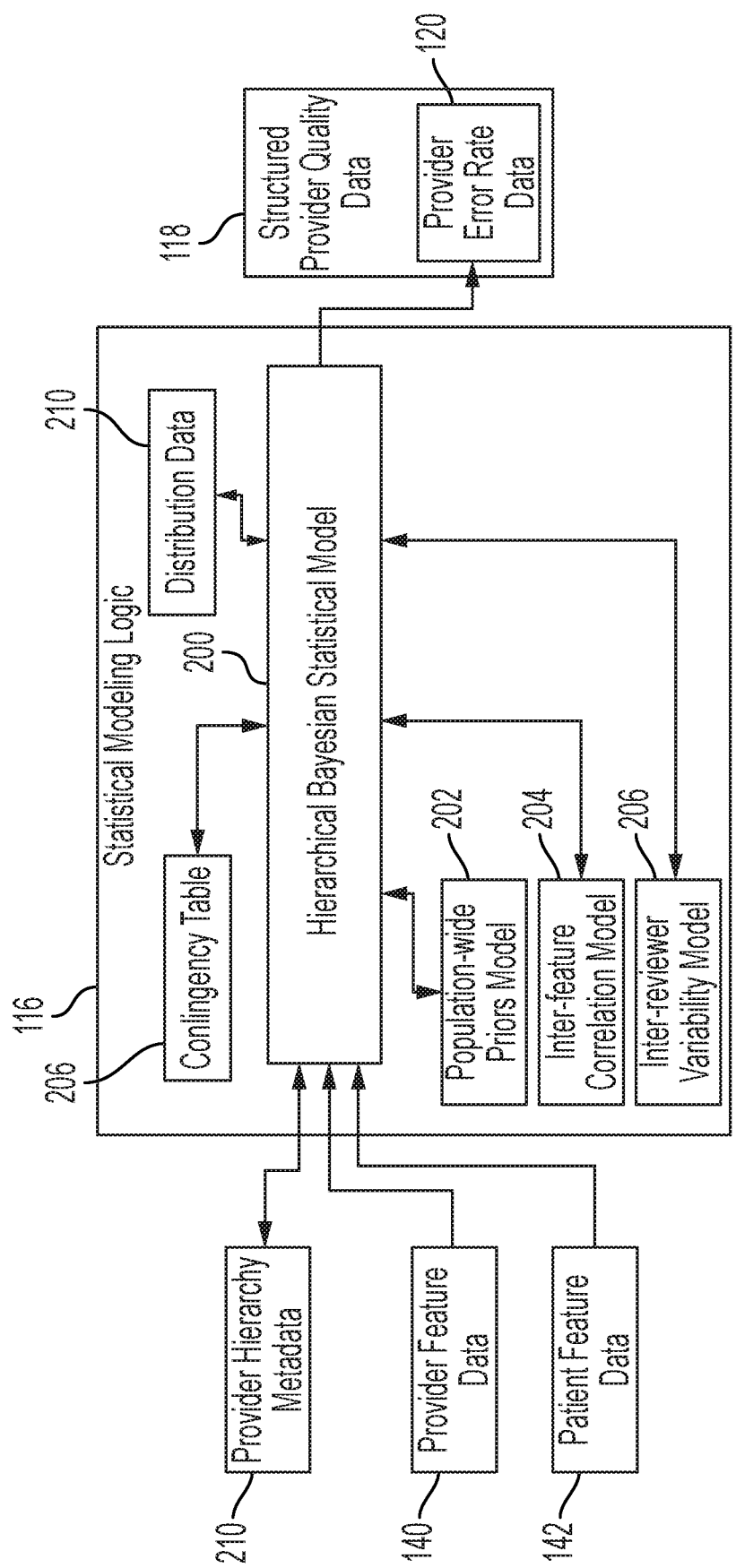
FIG. 2 illustrates further details of the statistical modeling logic of FIG. 1.
Figure 3:
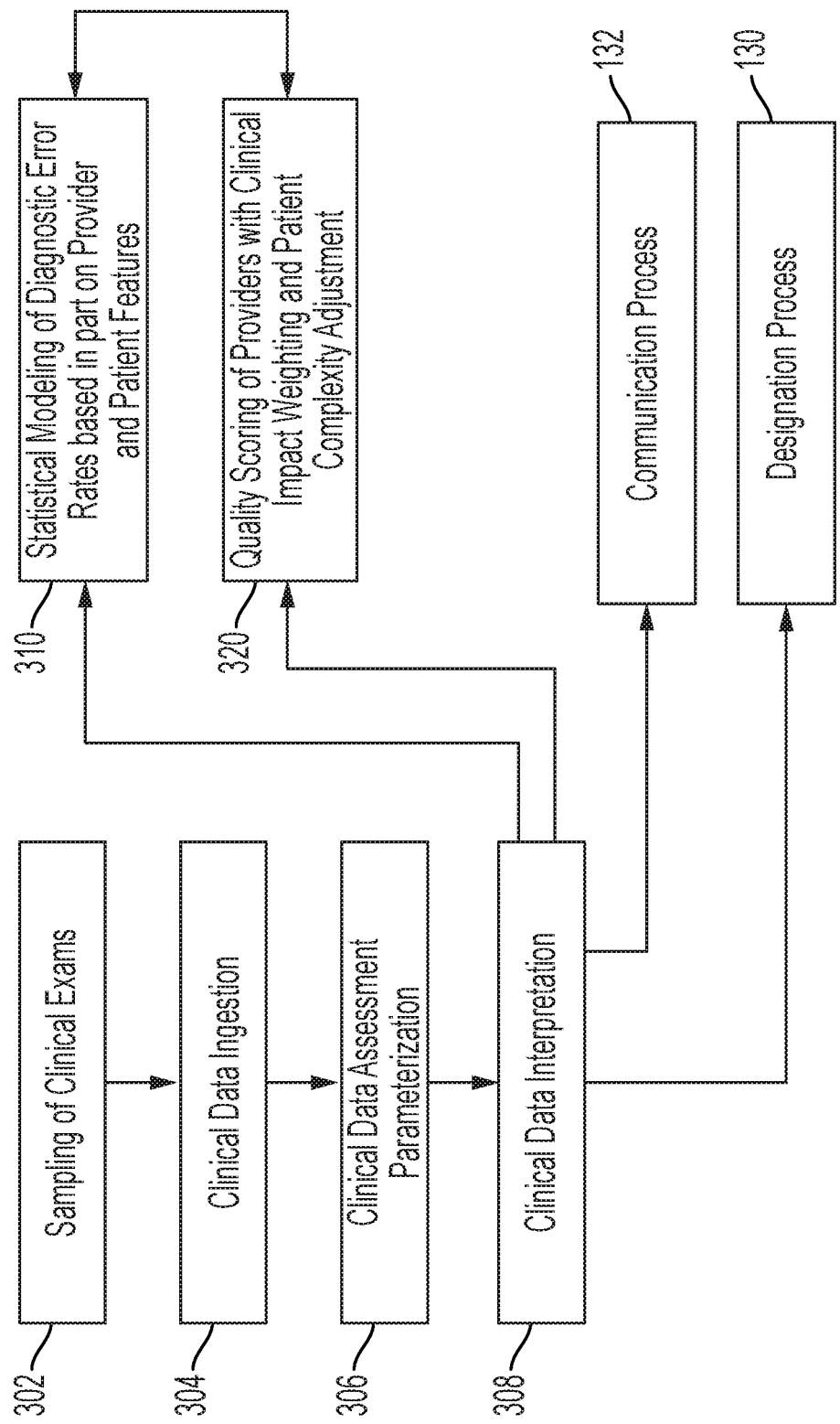
FIG. 3 illustrates an example data assessment process that may be used in an embodiment.

The system that has been generally described with reference to FIG. 1 may be used for estimating true diagnostic error rates via statistical algorithms. FIG. 2 illustrates further details of the statistical modeling logic of FIG. 1. FIG. 3 illustrates an example data assessment process that may be used in an embodiment. Referring first to FIG. 2, in one embodiment, the statistical modeling logic 116 is programmed to execute a hierarchical Bayesian statistical model 200. All elements of statistical modeling logic 116 are implemented using one or more computer programs, methods, web services, microservices and/or other software elements.

In an embodiment, foundation methodology for the statistical model 200 is to reduce outliers, narrow confidence intervals and improve the accuracy of estimates of true diagnostic error rates based on observed samples, especially for rarer types of diagnostic errors. In an embodiment, statistical model 200 uses a population-wide priors model 202, inter-feature correlation model 204 and inter-reviewer variability model 206. In an embodiment, the inter-reviewer variability model 206 is programmed to assess the reliability and consistency regarding the detection and measurement of specific types of diagnostic errors by reviewers. Its output may be used to assign confidence interval values and probability values to the provider error rate data 120 (FIG. 1). Statistical model 200 may store and use a contingency table 208 and distribution data 210 comprising one or more statistical distributions that are calculated as interim steps, as further described in this section.

In an embodiment, inter-feature correlation model 204 is programmed to use statistical techniques to characterize the correlation between groups of features. For example, groups of diagnostic error rates may be correlated; examples might be errors related to all lumbar spine pathologies, or the relationship between all diagnostic error rates of the type "overcall" to all diagnostic error rates of the type "undercall".

In an embodiment, the inter-reviewer variability model 206 is programmed to execute the seven-step process described above for parameterization logic 112, for a subset of exams consisting of associated digital images 104 and reports 105, for a plurality of different reviewers and to assess the level of agreement or disagreement of different reviewers, yielding an inter-reviewer variability score value. The inter-reviewer variability score value may be used as a factor in the statistical modeling logic 116.

In an embodiment, integration of provider feature data 140 and patient feature data 142 can further improve the estimate of true diagnostic error rates and can allow for estimates of diagnostic error rates for which the database 107 stores limited to no observed error rates. In the case of radiology, examples of features that can be represented in provider feature data 140 comprise educational history, size of practice and type of imaging equipment. Examples of features that can be represented in patient feature data 142 are age, sex, other demographic values and diagnosis.

Statistical model 200 also may receive provider hierarchy metadata 210, from database 107 for example. The provider hierarchy metadata 210 enables statistical model 200 to factor in the hierarchical structure of a healthcare provider. For example, provider hierarchy metadata 210 may specify that a particular provider is a practice, facility, individual physician or radiologist, or reflect other hierarchical levels or categories. In some embodiments, features of each entity represented in provider hierarchy metadata 210 include practice data such as size and academic affiliation; facility data such as type of imaging equipment and imaging protocols that are used; physician data such as years in practice and training attributes; and reviewer data such as years in practice and training attributes. Provider hierarchy metadata 210 may be created and stored for all the providers that are assessed using the computer system 10. The use of provider hierarchy metadata 210 enables statistical model 200 to differentiate and cross-relate features at the appropriate hierarchical level for each entity, thereby allowing for the most accurate estimate of true diagnostic error rates achieved by various practitioners.

In one embodiment, statistical model 200 is programmed to execute the following capabilities:

A. Estimation of the prevalence of diagnosis co-occurrence, via diagnosis co-occurrence statistical modeling.

B. Modeling of the agreement between reading provider and reviewer provider for a diagnosis at the item level, including: estimation of item-level diagnostic accuracy; calibration of the uncertainty of the "gold" standard diagnoses from reviewing providers using variability and inter-reviewer agreement measurements that are calculated from the data generated when multiple reviewing providers assess the same radiology exams and examples of the same pathologies and diagnostic errors.

C. Impact and significance mapping.

D. Item panel accuracy dependence.

E. Provider surveillance including modeling checklist levels and determining definitions of non-specific providers and adjustable providers.

F. Predictive extrapolation.

G. Information sharing and data pooling capabilities, including segmentation of provider populations, hierarchically informed estimation of population, and parsimonious inferential specifications.

In one embodiment, statistical model 200 is programmed to execute, using the computer system 10, functions that may be expressed for convenience in the following mathematical notation.

$$f\Big(R_{1l},\ldots,R_{pl},\tilde{R}_{1l},\ldots,\tilde{R}_{pl},D_{1l},\ldots,D_{pl},\theta_{1l},$$
$$\ldots,\theta_{pl},\mu,\sum\nolimits_{\theta}\mid X^{(R)},X^{(\tilde{R})},X^{(D)}\Big)=f(R_{1l},\ldots,R_{pl}\mid X^{(R)})\times$$
$$\prod_{i=1}^{p}f\big(D_{il}\mid \tilde{R}_{il},X^{(D)},\theta_i\big)f\big(\tilde{R}_{il}\mid R_{il},X^{(\tilde{R})}\big)f\big(\theta_i\mid \mu,\textstyle\sum_{\theta}\big)\times f\big(\mu\mid \textstyle\sum_{\theta}\big)$$

The expression above provides fully integrated probability characterizations of modeling specifications that are next described. Each component of the notation above represents a well-defined statistical estimation context. A Bayesian approach provides an optimized way to simultaneously address full uncertainty propagation and characterization at all data levels; incorporation of inherently unobserved measurements into the analysis; and flexible information pooling capabilities to permit identifying and representing the parsimonious dependency characteristics of the foundation data.

In an embodiment, the function $$f(R_{1l},\ldots,R_{pl}\mid X^{(R)})$$

yields a log-linear contingency table represented in FIG. 2 as contingency table 208. The function provides a co-occurrence distribution of reviewing provider diagnoses $R_{1l},\ldots R_{pl}$ for p items at location l with risk adjustment for features $X^{(R)}$.

In an embodiment, the function $$f(D_{il}\mid \tilde{R}_{il},X^{(D)},\theta_i)f(\tilde{R}_{il}\mid R_{il},X^{(\tilde{R})})$$

provides a reading provider diagnosis distribution $D_{1l}$ for item I given uncertain true diagnosis $\sim R_{1l}$ given reviewing provider diagnosis $R_{1l}$. The component expression $$f(D_{il}\mid \tilde{R}_{il},X^{(D)},\theta_i)$$

represents a multi-class classification conditional on unobserved $\sim R_{1l}$. Performance of $D_{1l}$ relative to $R_{1l}$ provides item-level accuracy estimation, while integration over $\sim R_{1l}$ incorporates "gold standard" uncertainty into the model. Furthermore, the component expression $$f(\tilde{R}_{il}\mid R_{il},X^{(\tilde{R})})$$

represents a categorical distribution capturing the observable variation in $R_{il}$. Observable variation in $-R_{il}$ is identified directly through repeated measures of multiple reviewing providers within specific checklists, as well as parametrically estimated across the population of all relevant checklists.

In an embodiment, an expert informed and healthcare impact driven score value may be derived by calculating:

$$g_k(R_{1l},D_{1l},\ldots,R_{pl},D_{pl}\mid E_k,Y_k)$$

in which the function $g_k$ is defined on the basis of both expert opinion elicitation ($E_k$) and empirical evidence ($Y_k$) and aggregates accuracy portfolios into scores characterizing performance with respect to specific (k-th) financial and care outcomes.

In the expressions above, $\theta_i$ is a feature-driven, hierarchically informed parameter that is specific to $D_{1l}\mid \sim R_{1l}$, $X^{(D)}$. The structure and degree of dependence between $\theta_i$ (i=1, ... p), e.g., ($\theta_1, \ldots \theta_p$) approximates $f(\mu, \Sigma_\Theta)$ explicitly models and drives accuracy dependency across item panels; the specification of this form addresses appropriateness and validation of the model.

In the expressions, $X^{(D)}$ may denote a provider or features characterizing providers, which allows for non-specific provider aggregations. Particular $\theta_i$ specifications reflect $X^{(D)}$ and capture associations attributable to $X^{(D)}$ while informing estimation across I via dependency structure in $\theta_i$.

Predictive extrapolation is available through standard $X^{(D)}\theta_i$ linear form inference.

Mixture model or post-hoc subpopulation segmentation provides aggregation driven estimation. Structure and dependency across $\theta_i$ provides hierarchical information pooling and sharing. Parsimonious feature engineering in log-linear model and multi-class classification contexts addresses infeasible saturated model approaches.

Mathematical notation has been used to describe embodiments herein for conciseness and convenience, and because it is the preferred language for communication between data scientists at the level of skill contemplated by this disclosure. However, nothing in this disclosure is intended to legally claim the use of mathematical functions or notations per se, in the abstract. Instead, the mathematical notation used herein is intended as a guide for skilled data scientists or others to program one or more computer programs to realize a practical application of the concepts that have been expressed. While numerous practical applications are described in other sections, in general, programs based on the mathematical notation herein may be applied to receive digital data representing physical anatomy or pathological reports, transform or classify the data, and generate output representing error rates and scores.

Referring now to FIG. 3, in one embodiment, the foregoing processes may be implemented using a feedback-oriented process starting at block 302 at which a sampling of clinical exams is performed. Block 302 may comprise executing the functions of sampling logic 106 (FIG. 1) that have been previously described, including all alternatives and variations.

At block 304, clinical data ingestion is performed. Block 304 may comprise executing the functions of clinical data ingestion logic 108 that have been previously described, including all alternatives and variations.

At block 306, clinical data assessment parameterization is performed. Block 306 may comprise executing the operations of structured assessment logic 110 as previously described, including all alternatives and variations.

At block 308, clinical data interpretation is performed. Block 308 may involve executing the operations of clinical data interpretation logic 114 as previously described, including all alternatives and variations.

At block 310, statistical modeling of diagnostic error rates based in part on provider features and patient features is performed. Block 310 may comprise executing the operations of statistical modeling logic 116 as previously described, including all alternatives and variations.

At block 320, quality scoring of providers with clinical impact weighting and patient complexity adjustment may be performed. Block 320 may comprise using structured provider quality data 118, including provider error rate data 120, with grading algorithm 122 and the weighting and patient complexity adjustment that have been described, to yield output provider quality scores 128, as previously described, including all alternatives and variations. Furthermore, the quality scores 128 may be provided as an element of feedback to block 310 to improve training and refinement of the statistical modeling logic 116.

4. Designation of Providers Based on Quality Scoring

In an embodiment, designation process 130 (FIG. 1) may be programmed, or used manually, to create and store designations of healthcare providers based on thresholds, a hierarchy or a ranking or labeling system. In one embodiment, radiology providers may be designated as high quality providers or Centers of Excellence based on the output provider quality scores 128 that are generated for the providers. Designations may be generated based on absolute values of the quality scores 128 or based on the scores in relation to later or downstream outcomes that are observed in patient populations. In some embodiments, data for outcomes for this purpose may be obtained from medical insurance claims records.

The designation process 130 may determine designations based on criteria such as comparison of quality scores 128 to thresholds derived from national benchmark data or regional benchmark data. The benchmark data may be stored in database 107 and may be determined over time by the computer system 10, by computing quality scores 128 for a plurality of providers and storing the score values in the database in association with provider identifying data that specifies geographic location. Thereafter, the score values may be sorted and grouped by region or nation to derive mean, median or other statistically significant values for providers in a particular group, region or nation. Then, a new quality score 128 generated for a particular provider can be compared to the benchmark for a region or nation in which that particular provider is located; if the new quality score passes a threshold value corresponding to the benchmark value, then a particular designation may be created and stored, or awarded.

These techniques are expected to permit assigning a designation with a high degree of statistical confidence. In some embodiments, the processes described in section (2) and section (3) of this document may be repeated on an ongoing basis to monitor the performance of providers over time, recalculate provider error rate data 120 and regenerate output provider quality scores 128 for the same providers. Ongoing repetition and recalculation in this manner is expected to further increase confidence levels associated with scores and designations.

5. Communication Processes

In some embodiments, communication process 132 (FIG. 1) may be programmed using presentation layer logic of computer system 10 to generate performance reports or dashboards that contain applications of the information generated via section (2) and section (3). The communication of provider error rate data 120, output provider quality scores 128, designations and/or data distilled from these values is expected to induce providers to elevate the standard of care that they provide.

6. Technical Benefits

Embodiments have been described that provide data-driven, objective assessment of healthcare provider diagnoses with the benefit of generating error data and quality scores that have not been available previously.

Typically, radiology or other healthcare quality measures are based on easily accessible proxy measures of medical care quality that focus on: process or workflow (e.g. average time between stroke patient arrival at provider facility and start of stroke treatment), structure (e.g. percentage of CT exam images and reports that providers make available to unaffiliated providers for the purposes of prior study comparisons), patient safety or outcomes (e.g. death rate of patients undergoing carotid artery stenting procedures), or subjective patient satisfaction surveys (e.g. patient feedback on wait times or physician bedside manner). These approaches to radiology quality measurement do not directly assess the quality of the medical care with respect to the accuracy of the imaging exams' diagnoses and rates of diagnostic errors.

The few examples of radiology or other quality measures that do focus directly on diagnostic accuracy and diagnostic errors, require a "gold standard" secondary medical test to be available for comparison, for example, the measure of mammography exam false positive rates that is defined by the Mammography Quality Standards Act (MQSA) of 1992 requires providers to compare positive mammography exams results to subsequent results of biopsy tests. This approach to quality measurement is not generalizable to most diagnostic imaging exams and exam types because secondary diagnostic tests are not routinely performed and available for comparison with the diagnostic imaging exam report.

Some formal peer review-based quality assessment programs have been proposed for use in radiology provider organizations, for example the American College of Radiology (ACR) has proposed the "RadPeer" program in which radiologists review a sample of radiology exams performed by other radiologists in their organizations and assign a subjective summary quality score of 1a, 2a, 2b, 3a, or 3b, to indicate if the overall quality of the diagnostic imaging exam under review achieved satisfactory or unsatisfactory quality and whether any diagnostic errors that are present are likely to have a clinically significant impact on the patient. This approach to quality measurement suffers from deficiencies that include: quality scores that do generalize across provider organizations, low levels of reproducibility, and quality scores that do not include any information on rates of specific types of diagnostic errors. These subjective peer review-based methods do not systematically capture information on the levels of inter-reviewer variability associated with specific aspects of the imaging exam quality assessments, and therefore: (1) are not able to appropriately weight attributes based on the confidence that specific diagnostic errors are present, or (2) supply appropriately confidence intervals around quality measures. Further, since peer reviewed methods like these only require the reviewing radiologist to assign a single summary quality score to each exam under review, and do not generate any granular or detailed information on specific types of diagnostic errors, they are not suitable for integration with computer-implemented machine learning methods.

Unlike existing radiology quality measurement systems, the embodiments described here produce radiology quality measures that: (1) are not proxy measures of clinical care quality and instead focus directly on the quality of diagnostic imaging care (i.e. diagnostic accuracy and rates of diagnostic errors), (2) do not require a secondary diagnostic test like a biopsy to be available to serve as a "gold standard comparison", and (3) are not based on subjective summary assessments from peers within the same provider organization and instead captures quality assessment data in a structured, granular and systematic manner that allows robust and reliable quantification of diagnostic error rates and associated confidence intervals.

Finally, the framework described here, in which structured data attributes related to diagnoses and diagnostic errors are generated from each exam quality assessment review, enables: (1) the method to be scaled and supplemented using machine-implemented algorithms that are trained using the reviewer-generated attributes, and (2) for correlations between the structured data attributes and additional provider attributes to be characterized, which allows measures of diagnostic error rates or weighted diagnostic error rates to be generate with improved accuracy and precision and generated for radiology providers which have not had any of their imaging exams subjected to standardized reviews (for whom only the supplementary data elements and attributes are available).

Consequently, the techniques herein provide opportunities for peer improvement by exposing objective and detailed factors that affect quality, rather than leaving medical disciplines to operate in an environment in which practices do not know why a particular practitioner has a high or low error rate, or may be associated with patients who experience better or worse healthcare outcomes. Instead, data features exposed in the present techniques provide reliable and robust measurements of error rates. This evidence can provide reasons to improve a practice's equipment, procedures, types of exam routing or other issues.

7. Natural Language Processing (NLP) Pipeline—General Overview

In order to achieve the broader goal of regressing to an estimation of the number of diagnostic errors made by radiologists, a comparison must be made between the clinical findings as they are interpreted from diagnostic imaging by a reviewing physician or radiologist (i.e. the individual who views the radiological images obtained from a patient's exam and then prepares a report summarizing his or her findings based on those radiological images) on one hand, and on the other, the actual ground-truth pathologies or abnormalities present in the same diagnostic imaging.

Accordingly, aspects of the present disclosure are directed to systems and methods for producing structured reports or other data outputs in which a defined set of pathologies are marked as present or absent from an input section of text from a radiological report. In some embodiments, the systems and methods include a Natural Language Processing (NLP) pipeline trained to analyze and transform input radiological report text into a plurality of word embeddings, wherein the word embeddings are further used to generate the aforementioned structured reports or other data outputs.

8. Natural Language Processing (NLP) Pipeline—Architecture Details

Disclosed is an NLP (or natural language understanding) pipeline trained to read and accurately analyze radiology reports inputted in any format. The disclosed NLP pipeline is able to extract more than just the most extreme diagnoses for a given pathology, and advantageously provides greater granularity of analysis and a corresponding ability to detect, when coupled with a computer vision pathology detection, more nuanced (but nevertheless common) diagnostic errors that would otherwise be missed or remain undetected. Moreover, aspects of the disclosed NLP pipeline provide the ability to classify, detect, or otherwise note where a given pathology is supposed to be located in a radiological image (i.e., according to the input radiological report text that was prepared based on the radiological image), thereby improving the speed and accuracy with which the diagnostic quality of input radiological reports can be verified against their corresponding radiological images, including via one or more automated machine learning techniques.

Notably, the disclosed systems and methods for an NLP pipeline provide an improved and efficient approach to training data generation, for example by utilizing a radiological report in piece-wise fashion rather than treating the entire radiological report as a single training data point. For example, it is often the case that a single radiological report contains multiple, distinct sentences or statements about a single pathology. Moreover, it is also commonplace that a single radiological report contains statements about several different pathologies. Accordingly, aspects of the present disclosure leverage radiological reports to generate multiple points of training data, e.g., from single sentences and/or from sets of sentences relating only to the same identified pathology. In this manner, the training process can separate the need for the NLP pipeline (or constituent machine learning model(s)) to learn to detect relevant sentences from the need to learn to interpret those sentences—unlike conventional approaches which force models to learn to detect relevant sentences while also learning to interpret those sentences. In this manner, aspects of the present disclosure achieve a training process that is more efficient and time expedient, and which also yields a more accurate final product, i.e., the trained NLP pipeline and its constituent machine learning model(s).

Figure 4:
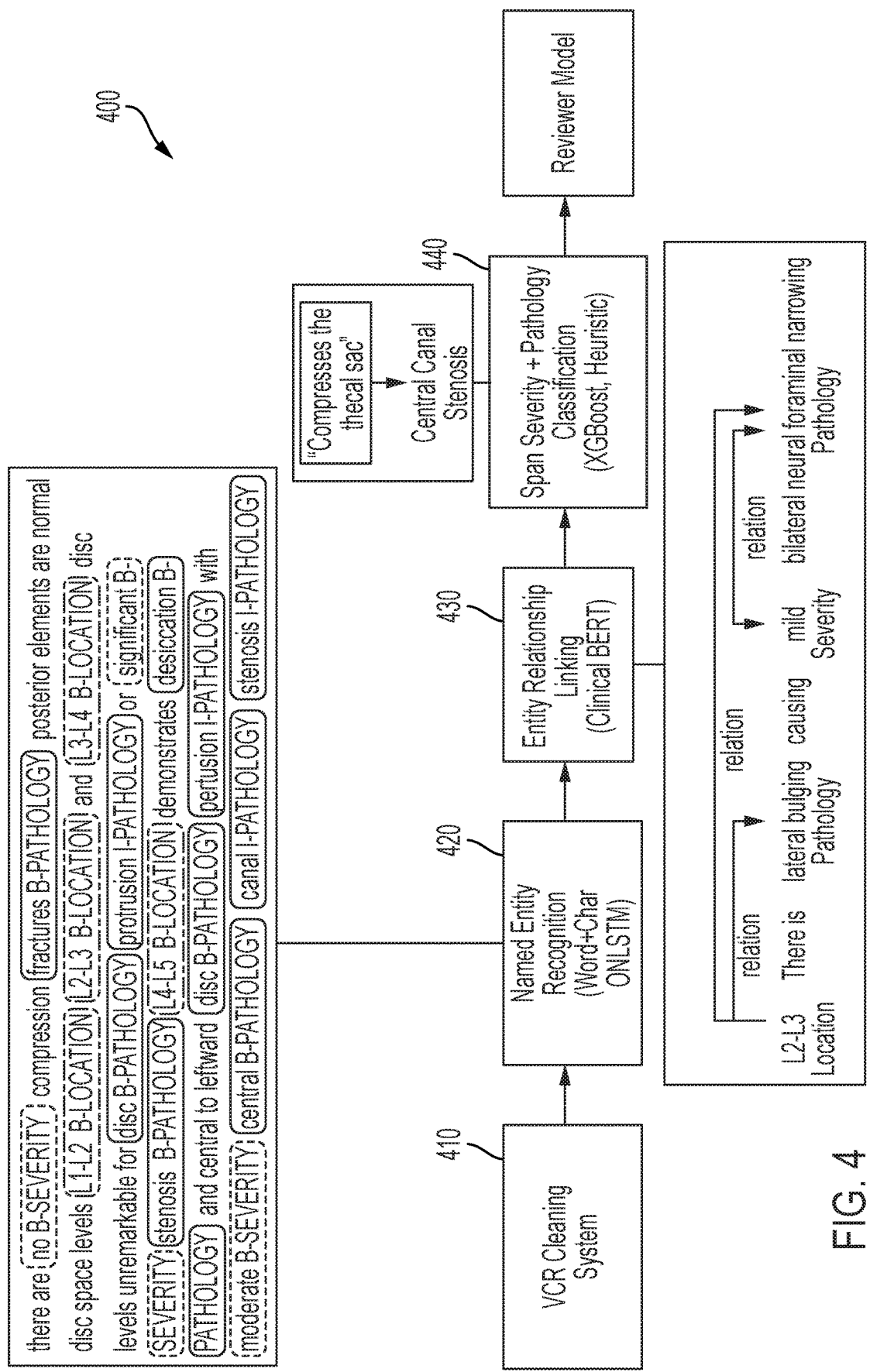
FIG. 4 illustrates an architecture diagram for an example NLP (Natural Language Processing) pipeline, according to aspects of the present disclosure.

The disclosure turns now to FIG. 4, which depicts an architecture diagram for an example NLP pipeline 400 according to aspects of the present disclosure. As illustrated, the architecture of NLP pipeline 400 includes an OCR cleaning system 410, a named entity recognition (NER) system 420, an entity relationship linking system 430, an entity classification system 440, and a reviewer model x50. However, it is appreciated that the various functionalities attributed to these individuals models as discussed below can be modified in terms of their assignment to a particular model or another and/or in terms of their order of operations, without departing from the scope of the present disclosure.

OCR Cleaning System 410

The discussion turns now to OCR cleaning system 410, which in some embodiments is configured to optimize, clean and error-correct an OCR output obtained from one or more OCR engines for a given input text. In particular, in the context of the present disclosure, it is contemplated that the input text provided to the one or more OCR engines, and therefore provided to OCR cleaning system 410, can be obtained from a radiological report. The text of these radiological reports indicates clinical findings as they are interpreted from diagnostic imaging by a reviewing physician or radiologist (i.e. the individual who views the radiological images obtained from a patient's exam and then prepares a report summarizing his or her findings based on those radiological images). The entirety of the radiological report can be provided to the one or more OCR engines, or the radiological report can be segmented or divided into sections, one or more of which can then be provided to the one or more OCR engines, either sequentially or in parallel.

Advantageously, noisy and inconsistent data are removed from the OCR output(s) before being provided to downstream components of NLP pipeline 400. For example, this OCR cleaning process thereby limits, or even prevents downstream machine learning networks from being forced to learn common misspellings, human errors, or other peculiarities that might otherwise have been present in a non-error corrected OCR output. Moreover, the disclosed OCR output cleaning process can reduce unnecessary and unwanted variance in the OCR output data, which reduces the need to design or train systems that are themselves robust to such noise—by reducing computational complexity or overhead, the presently disclosed NLP pipeline 400 is able to provide the same or greater robustness, but in a more lightweight form.

Radiology reports can be obtained in a variety of different formats, including but not limited to digital text files, digital document files (e.g., PDFs), digital image files of printed text (e.g., a scan of a printed radiological report or notes), digital images files of handwritten text (e.g., a scan of a handwritten radiological report or notes), etc. In general, radiology reports that are represented only as a digital image file or scan are the most challenging format of input data to parse and process for subsequent use in the NLP pipeline 400 and/or subsequent machine learning networks that assess the diagnostic quality between the radiological report text and the underlying radiological exam images from which the radiological report was derived. In some embodiments, radiology reports that are received as a digital text file, rather than as a scanned image, can bypass OCR cleaning system 410 and be passed directly to named entity relationship linking system 420.

When a radiological report is received at OCR cleaning system 410, it is first fed into one or more OCR engines, which generate one or more initial OCR outputs, where each initial OCR output is a digital text representation of the words detected by the OCR engine in the input radiological report. The one or more OCR engines can include, but are not limited to, Tesseract, AWS Textract, and Acrobat OCR. In some embodiments, the set of initial OCR outputs from each OCR engine can be analyzed to determine which version is best for the particular input radiological report, as well as to detect and correct common errors introduced by the OCR engines. The cleaned OCR output that is determined to be the best for the input radiological report is then passed to entity relationship linking system 420.

OCR cleaning system 410 can employ several different techniques to perform the aforementioned detection and correction of error(s) introduced by the OCR engines. For example, a Levenshtein distance spellchecking algorithm can be augmented to account for optical transformation costs of character pairs. The Levenshtein distance measures the difference between two words as the minimum number of single-character edits required to change one word into the other word. Spell-checking is then performed by analyzing the Levenshtein distance from a misspelled word to a dictionary of words—replacement is performed on the assumption that the most frequently occurring dictionary word with the smallest Levenshtein distance is most likely to be correct. In some embodiments, OCR cleaning system 410 can supplement Levenshtein distance calculations with a library of optical transformation costs and/or can supplement the dictionary frequency analysis with specific word-frequency dictionaries for each type of radiological exam.

Although Levenshtein distances are calculated via a character-level analysis, the analysis weights all single-character edits equally, i.e. the transformation cost from 'u' to 'v' is the same as the transformation cost from 'u' to 'z'—in both cases, the cost is 1. Accordingly, OCR cleaning system 410 augments its spellchecking approach by using a library of optical transformation costs to more accurately weight or otherwise supplant certain Levenshtein distance costs. For example, the transformation of 'm' to 'ni' has a Levenshtein cost of 2, but in the augmentation library of OCR cleaning system 410, the same transformation is instead determined to have a decimal cost close to 0. Therefore, in a scenario in which an OCR engine determines that 'm' is the most likely candidate for a given input character being analyzed, followed by 'n', and then 'ni', OCR cleaning system 410 is able to identify that 'ni' is actually the most likely to be correct based on context—despite the fact that it is ranked as third most probable according to the OCR output from the OCR engine(s). The library of optical transformation costs can be calculated over a subset of different letter or character pairs, with a greater emphasis given to pairs that exhibit a significant reduction relative to their Levenshtein cost. Additionally, as indicated by the above example, the library of optical transformation costs can include both single letter transformations and multi-letter transformations.

Rather than using a general, English language dictionary or corpus to perform a word-frequency analysis, OCR cleaning system 410 can instead utilize one or more specific word-frequency dictionaries for the type of radiological exam that is represented by the input radiological report being analyzed. For example, an input radiological report might have been prepared for a lumbar spine MRI and can be analyzed against a specific word frequency dictionary for lumbar spine exams, for MRI exams, for lumbar spine MRI exams, or some combination of the three. In this manner, OCR cleaning system 410 performs a context-aware frequency analysis, boosting the ranking for potential replacement terms that may be common in the context of the radiological exam that was performed (e.g., "lumbosacral") but quite uncommon in the context of an overall English lexicon. The context-specific word-frequency dictionaries can draw on one or more domain-specific or clinical lexicons, including open-source clinical lexicons and repositories of clinical text(s).

In some embodiments, these context-specific word-frequency dictionaries can be generated from a plurality of existing radiology reports, e.g., where the existing radiology reports are stored or otherwise labeled with an indication of the context or type of exam represented in each report. For example, in some embodiments images of the radiology reports (or other digital/document representations of the radiology reports) may be the same as the physician diagnostic reports 105 that are stored in the database described with respect to FIG. 1. Similarly, a large portion of the training data needed to train NLP pipeline 400 and its constituent components and machine learning networks can be obtained by leveraging the already existing data stored in, for example, database 107 of FIG. 1, which significantly reduces the burdensome need of actively collecting, collating and annotating training data from scratch.

Returning to the discussion of OCR cleaning system 410, in some embodiments, OCR cleaning system 410 can generate a list of most probable correction candidates for an unknown word in the OCR output(s) received from the OCR engine(s). For example, the list of most probable correction candidates (e.g., the top five, ten, etc., results) can be determined as described above, where edit distances over a specific word-frequency dictionary are weighted by optical transformation costs.

OCR cleaning system 410 then selects from the list of correction candidates by analyzing the context in which the unknown word appears i.e., the word(s) immediately preceding and following the unknown word in a sentence or text fragment. Each correction candidate is used to replace the unknown word in the sentence, and the resulting sentence is then provided as input to a masked language model that determines which correction candidate produced the highest likelihood or probability score. In some embodiments, the masked language model is trained on biomedical word embeddings or Word2vec encodings (such as Word2vec embeddings obtained from http://bio.nlplab.org/, compiled over a corpus of PubMed articles). Based on the biomedical word embeddings, the masked language model of OCR cleaning system 410 can be used to determine semantic similarities and relationships between correction candidates and the context of the sentence into which it is inserted. For example, the masked language model can include a BERT (Bidirectional Encoder Representations from Transformers) model such as ClinicalBERT, or some other Transformer-based model that has been fine-tuned over a dataset of radiological reports and/or clinical terms. In some embodiments, the masked language model can be trained over the same radiology report corpus that is used to generate word-frequency dictionaries that are specific to certain types of radiological exams.

In some scenarios, the context surrounding an unknown word may still be insufficient to ascertain a spelling correction (i.e., to make a selection from the list of correction candidates) with a suitable or desired degree of certainty, or the biomedical word embeddings alone are otherwise of limited utility when provided as input to the masked language model of OCR cleaning system 410. Accordingly, the masked language model can additionally be trained on the clinical significance of mistaking certain words, based on both lexicon data and input from one or more clinicians (e.g., a panel of expert radiologists or reviewing physicians). In some embodiments, the previously described masked language model can be supplemented with additional context suggestions from one or more Transformer models (such as TinyBERT) that are trained to provide spatial and temporally efficient vocabulary substitutions based on document-level context (rather than the sentence-level context of the masked language model).

Named Entity Recognition (NER) System 420

The process of named entity recognition involves recognizing numerous domain-specific proper nouns, here in the context of a biomedical domain (or more specifically, in some embodiments a radiology domain). As illustrated, named entity recognition (NER) system 420 receives as input a digital representation of text, which can be provided as the output from OCR cleaning system 410, or in some embodiments can be provided directly to NER system 420, i.e., in scenarios in which the input radiological report is already stored in a digital text file format, OCR cleaning and correction is not necessary.

At the point of ingestion to NER system 420, the report text remains unstructured. NER system 420 is applied to begin the process of structuring the report text. In particular, NER system 420 locates and classifies named entities mentioned in the report text into pre-defined categories. For example, in the context of NLP pipeline 400 being used to process radiological reports, the pre-defined categories might be those that are of interest when making a diagnostic decision, e.g., a pathology or abnormality, its location, and its severity. Note that each of these categories of information can be captured by multiple words within contiguous spans of words (e.g. "Central Canal Stenosis" is a three-word span that represents a single pathology). Accordingly, NER system 420 is trained to identify word spans that can be grouped under the 'Pathology,' 'Location,' and 'Severity' classes.

In some embodiments, NER system 420 is configured to receive radiology report text, read the text sentence-by-sentence, and classify each individual word according to an IOB (Inside-outside-beginning) tagging scheme. In particular, IOB tags—indicating whether a given word marks the beginning 'B' of a named entity, is inside 'I' of a named entity, or is outside 'O' and belongs to no named entity—are used to construct the various named entities that will be grouped according to the 'Pathology,' 'Location,' and 'Severity' classes of NER system 420. It is noted that all named entities start with a 'B' under the IOB tagging scheme, regardless of whether the named entity consists of a single word or a contiguous span of multiple words. The T tag is applied only to named entities consisting of multiple words. For example, the pathology "central canal stenosis" would be tagged as T, T (or 'B—Pathology', 'I—Pathology', 'I—Pathology') whereas the pathology "fractures" would be tagged as 'B' (or 'B—Pathology').

In some embodiments, NER system 420 can implement an ordered neuron Long short-term memory (ON-LSTM) or other recurrent neural network trained to perform the IOB tagging. For a given sentence of report text, inputs to the ON-LSTM can include biomedical embeddings obtained for the individual words and character-level embeddings trained on a dataset of reference radiological reports. The biomedical embeddings obtained for the individual words can be the same embeddings as those mentioned previously with respect to OCR cleaning system 410, e.g., Word2vec embeddings obtained from http://bio.nlplab.org/, compiled over a corpus of PubMed and PubMed Central articles. In some embodiments, the biomedical embeddings can be refined by defining a subset of radiology-specific terms from the full biomedical Word2vec model, based on vocabulary that is actually present in a dataset of reference radiological reports (or some other dataset or corpus of radiology terms). For example, in some embodiments a full biomedical Word2vec model trained over a variety of medical publications and which is 13 gigabytes in size, can be reduced to only 170 megabytes in size when refining to include only radiology terms. Additionally or alternatively, biomedical embeddings can be obtained by training a custom Word2vec model over a corpus of radiology texts or reports, thereby yielding embeddings that are domain specific to radiology reports without requiring the aforementioned determination of a subset of a broader model.

Regardless of the source of the biomedical word embeddings, the word-level embeddings are treated as static while character-level embeddings are then learned over the corpus. These character-level embeddings are trained and optimized such that NER system 420 is better able to catch misspellings and any other OCR errors (e.g., complementary to the approach described above with respect to OCR cleaning system 410), thereby increasing the accuracy of the IOB tagging performed by the ON-LSTM and NER system 420 as a whole.

When iterating through a sentence of report text, the static biomedical embedding for each given word are obtained and concatenated with the optimized character-level embeddings for the same word (i.e., word and character embeddings are obtained and concatenated on a per-token basis by NER system 420). The concatenated embeddings are then provided as input to the ON-LSTM and classified using a Conditional Random Field (CRF). For each given token (i.e. word from the input sentence of report text), the CRF is trained to predict a classification or label while taking into account the context of neighboring samples. Because word and character-level embeddings are both utilized, rather than just word embeddings alone, the CRF achieves an improved accuracy in classifying the individual words of a radiology report according to the IOB tagging scheme. In some embodiments, certain transition probabilities can be configured as rules within the CRF in order to further enhance the accuracy of NER system 420 in detecting and classifying named entities within input radiology report text. As mentioned previously, named entities will always begin with a 'B' tag under the IOB tagging scheme, and therefore the T tag can only follow a 'B' tag or another T tag, but not an 'O' tag. Accordingly, the transition probability between an 'O' tag and an T tag can be set to zero within the CRF.

After the completion of the IOB tagging and classification process, NER system 420 provides as output a plurality of NER tagged spans, where each NER span (comprising either a single word, such as "fractures", or multiple words, such as "central canal stenosis") is tagged with an IOB tag and with an additional label according to the determined classes configured in NER system 420, i.e., as 'Pathology,' 'Location,' or 'Severity' in the context of the present example, although it is appreciated that other classification schemes can be employed with NER system 420 without departing from the scope of the present disclosure. Thus, as mentioned previously, the pathology "central canal stenosis" would be tagged and classified as: 'B—Pathology', 'I—Pathology', 'I—Pathology', whereas the pathology "fractures" would be tagged and classified as 'B—Pathology'.

Entity Relationship Linking System 430

Entity relationship linking system 430 first performs relation extraction or otherwise identifies pairs of potentially linked entity spans to provide to a sequence classification model, as is described in greater depth below. From the sequence classification model, entity relationship linking system 430 determines and identifies linking relations between named entities. As illustrated, entity relationship linking system 430 can receive as input the plurality of NER tagged spans from NER system 420—where each NER tagged span has been broadly classified as representing either a 'Pathology,' a 'Location,' or a 'Severity'—and can then identify semantic associations between the NER tagged spans. In particular, these semantic associations can reflect the nature of how radiology reports are written, wherein a single sentence might refer to a pathology, describe its location, and diagnose its severity. Accordingly, entity relationship linking system 430 is trained to identify semantic relationships between various nearby pairs of NER tagged spans, e.g. Pathology-Location relationships and Pathology-Severity relationships. In some embodiments, entity relationship linking system 430 can identify multi-level or tiered relationships, e.g., such as in the scenario in which two Pathology-Severity relationships are further linked to the same Location.

From these semantic relationships, a structured document is created to represent the set of relationship linkages that underly the plurality of NER tagged spans provided as input to the entity relationship linking system 430. Advantageously, by generating a structured relationship linkage document for the underlying radiological report (recalling that the input NER tagged spans are derived from a single radiological report, or section of a single radiological report), downstream systems and machine learning networks are able to focus only on the information from the radiological report that is relevant to their specific purpose(s). For example, the structured relationship linkage document can enable the pathology and severity noted in a radiological report for a certain anatomical location to be quickly obtained and analyzed against a radiological image depicting the certain anatomical location.

In some embodiments, entity relationship linking system 430 can include a machine learning model (also referred to herein as a "detection model") for each specific pair of NER span types. For example, a first detection model can be trained to identify Pathology-Location relationships in the plurality of NER spans and a second detection model can be trained to identify Pathology-Severity relationships across the same plurality of NER spans. In some embodiments, one or more of the detection models can be based on a BioBERT relation extraction methodology. BioBERT is a BERT model (Bidirectional Encoder Representations from Transformers) pre-trained specific to the biomedical domain, which performs classification over anonymized target entities in a sentence by using tags to mask the target entities.

In the context of the present disclosure, training data can be generated by extracting pairs of potentially linked NER spans (i.e., two NER spans that are nearby or adjacent, typically in the same full sentence). For each potential pair of NER spans, the continuous section of text that contains both of the NER spans is extracted from the underlying radiological report (i.e., the radiological report from which NER system 420 generated the NER spans). The two potentially linked NER spans are then each replaced with a mask, according to their type. For example, a Pathology-tagged NER span can be replaced with a "@PATHOLOGY$" mask, a Location-tagged NER span can be replaced with a "@LOCATION$" mask, and a Severity-tagged NER span can be replaced with a "@SEVERITY$" mask.

The continuous section of text might contain the two potentially linked NER spans and one or more additional NER spans. In some embodiments, the additional NER spans can be replaced with a secondary mask according to their type, e.g., "[pathology]", '[location]", and "[severity]". Notably, any secondary masks are distinguishable from the masks applied to the two potentially linked NER spans contained within the same continuous section of text.

Thus, to obtain training data, potential NER pairs are generated from a set of training NER spans and a segment of training text is generated for each potential NER pair according to the above masking convention. Each segment of training text is then fed to the appropriate detection model for classification, such that the classification output is trained to predict whether the two NER spans are linked (i.e., a segment of training text containing a "@PATHOLOGY$" mask and a "@LOCATION$" mask would be fed to the first detection model for pathology and location NER span combinations; a segment of training text containing a "@PATHOLOGY$" mask and a "@SEVERITY$" mask would be fed to the second detection model for pathology and severity NER span combinations). Each segment of training text can be annotated with a ground-truth label indicating whether or not the two NER spans are actually linked.

Figure 5:
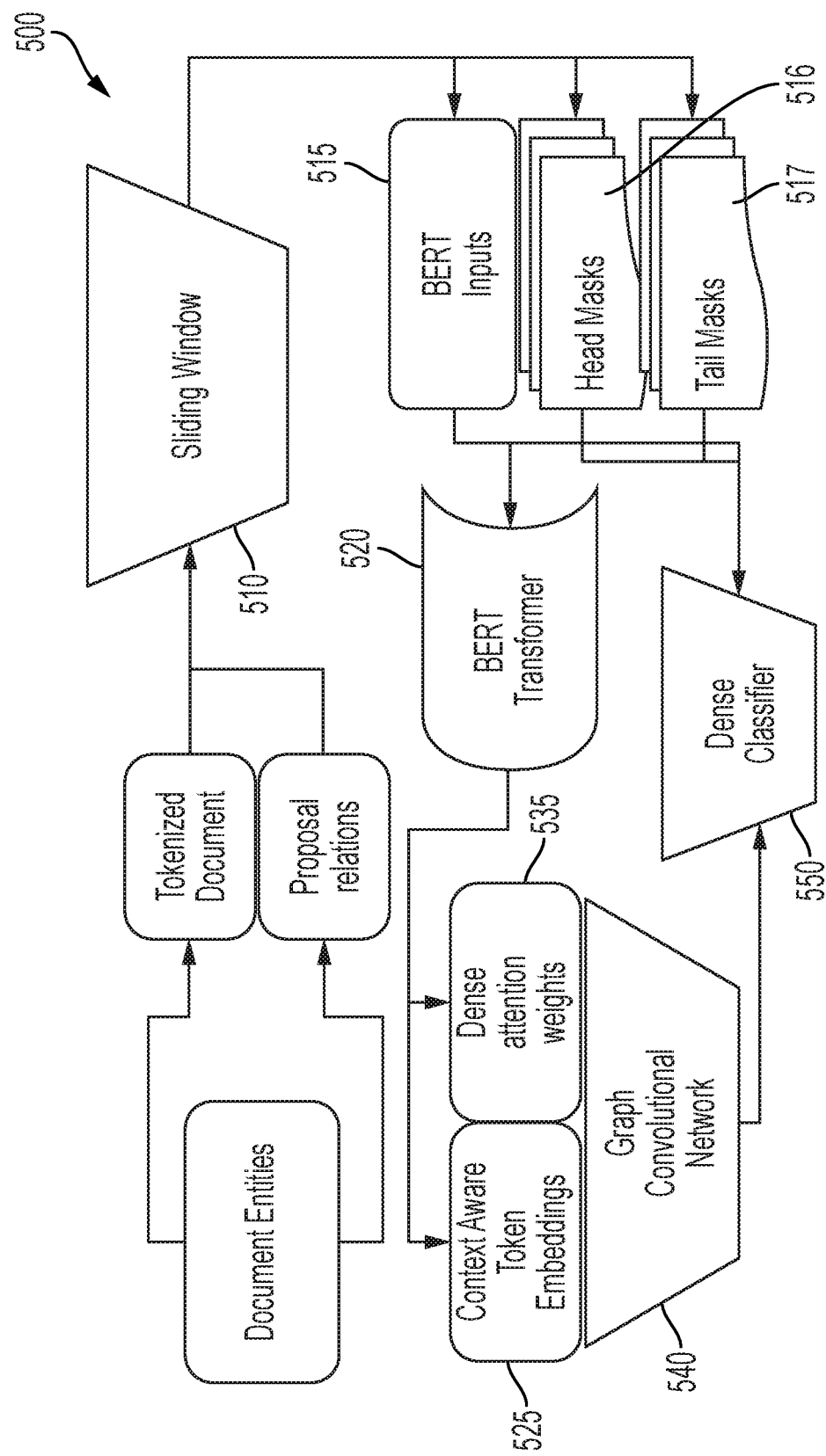
FIG. 5 illustrates an architecture diagram for an example entity relationship linking system, according to aspects of the present disclosure.

In some embodiments, classification can be performed based on a ClinicalBERT Transformer model, which can be further configured to have additional relationship-based features pertaining to the hidden representation of each masked NER span, as well as the attention weights between NER spans. FIG. 5 depicts an architecture diagram for an example entity relationship linking system 500, which in some embodiments can be similar or identical to entity relationship linking system 430. Unlike conventional approaches to relationship extraction, which struggle with problems or inputs having many potential relations clustered close together, the present disclosed entity relationship linking system 500 utilizes multiple relationship extraction techniques in a model that can efficiently classify all potential relations in a given span simultaneously.

In particular, entity relationship linking system 500 combines outputs from Transformer-based models (such as BERT Transformer 520) and Graph Convolutional Network (GCN) models (such as Graph Convolutional Network 540) into a single dense classifier 550. A sliding window 510 is used to send the same context through BERT Transformer 520 for each potential relation pair, wherein the context comprises the NER spans determined for the radiological report text input to NLP pipeline 400. As described above, sliding window 510 generates a plurality of BERT inputs 515 from the NER spans by slightly altering each BERT input to mark (mask) the relations of interest, i.e., the potentially linked NER spans for evaluation. Head masks 516 and tail masks 517 are also obtained from sliding window 510, for later use as inputs to the dense classifier 550.

Each of the plurality of BERT inputs 515 are sent through BERT Transformer 520, which can be pre-trained over a biomedical corpus and in some embodiments, fine-tuned over a radiology-specific corpus. Bidirectional input encodings and a dense adjacency matrix are then derived from the outputs and attentions of BERT Transformer 520, as it processes the plurality of BERT inputs 515. As depicted in FIG. 5, context-aware token embeddings 525 and dense attention weights 535 are provided as inputs to graph convolutional network (GCN) 540. Notably, and advantageously, the attention weights 535 measured for the BERT Transformer provide a dense adjacency matrix without relying on a slow and potentially erroneous dependency parse, as would otherwise be required to perform graph convolution on its own.

Based on the context-aware token embeddings 525 and dense attention weights 535, GCN 540 therefore is able to generate relation-pair specific features for the proposed relationship between NER spans, e.g., the relation-pairs as represented in each individual one of the plurality of BERT inputs 515. As depicted at dense classifier 550, the relation-pair specific features from GCN 540 are aggregated across corresponding head mask(s) 516 and tail mask(s) 517 in order to generate the ultimate output prediction indicating whether, and to what extent, two given NER spans are linked. In some embodiments, the architecture of entity relationship linking system 500 can be expanded using BERT-AL (BERT for Arbitrarily Long Document Understanding), such that entity relationship linking system 500 can be trained to operate on an entire input document at once, without any overlapping inputs such as those generated from sliding window 510. In this manner, entity relationship linking system 500 is able to analyze an entire input radiological report text (or section thereof) without having to perform piecewise analyses of potential relation-pairs between NER tagged spans.

Entity Classification System 440

While NER system 420 identifies various NER spans and tags them with a broad category of interest (e.g., 'Pathology,' 'Location,' or 'Severity'), additional details are often needed in order to extract clinically relevant information via NLP pipeline 400. In other words, although an NER tagged span might be broadly classified as a 'Pathology,' it is still necessary to determine the specific type of pathology that is indicated by the NER tagged span. This can be particularly necessary in instances where non-standard terminology is used in the underlying radiology report. For example, NER system 420 might generate a Pathology-tagged span "compresses the thecal sac"—words that do not directly state a pathology type themselves, but rather describe the manifestation of a pathology type. Accordingly, in this example entity classification system 440 would classify the "compresses the thecal sac" Pathology-span as Central Canal Stenosis.

In general, entity classification system 440 is trained to classify the NER tagged spans with one or more additional, detailed attributes. In this manner, variations in language and description as found in the underlying radiological reports can be eliminated or minimized, and the NER tagged spans can be classified according to a consistent and cohesive terminology framework. One approach to training entity classification system 440 involves manually labeling an entire set of NER tagged spans with their appropriate detailed attributes, e.g. in the context of the example above, one training data point would consist of the Pathology-tagged span "compresses the thecal sac" and a label "Central Canal Stenosis." However, such a process can be cumbersome and time-consuming in order to build a sufficiently large training data set that covers the desired space of detailed attributes. Accordingly, in some embodiments, the generation of training data for entity classification system 440 can be optimized to significantly reduce the number of NER spans that need to be labeled or annotated.

In some embodiments, the optimization of training data annotation and generation can be performed in an iterative fashion. For example, entity classification system 440 can be pre-trained on the previously discussed set of biomedical Word2Vec encodings (and/or any radiology-specific encodings or clinical lexicon(s), as also discussed previously), thereby providing a starting framework from which entity classification system 440 can be further trained and refined to classify each NER tagged span in accordance with a consistent terminology. In this scenario, prior to any labeling, entity classification system 440 uses the pre-trained encodings to perform a first-pass annotation of the sample set of NER tagged spans. The set of NER tagged spans and the results of the first-pass annotation are then analyzed in order to identify specific spans that will provide the greatest performance improvement from being labeled for the next training iteration of entity classification system 440. In other words, training data is generated by labeling the NER spans that the analysis determines will provide the greatest marginal improvement not only in the specific classification model(s) of entity classification system 440, but also the greatest marginal improvement in the performance of NLP pipeline 400 as a whole. In this fashion, the generation of training data (i.e. labeled NER spans) can be optimized iteratively and/or concurrently with the overall training of entity classification system 440.

The analysis upon which the selection of specific NER spans for annotation is based takes into account a variety of factors, including but not limited to the similarity of already existing annotations and entity classification system 440's prediction confidence for an NER span being considered for annotation. Recall that NER system 420 reduces sentences of radiological report text into NER spans, which can be as short as a single word. On this basis, many NER spans are found to repeat over the training data set. By identifying duplicates and applying word frequency metrics, almost all possible NER span phrasings for a set can be covered by annotating a selected ~1% of the set of NER spans. Word frequency metrics can additionally be used to identify rare words (i.e. low frequencies of occurrence) combined with high feature weights on those words in the classification model(s) of entity classification system 440, which suggests a need for augmented training data to be added. Accordingly, NER spans containing infrequently used words having high feature weights can be selected for annotation. Additionally, the analysis can be further based on an iterative accuracy of the full NLP pipeline 400, for example by creating an increased preference to annotate NER spans that were involved in an incorrect output from NLP pipeline 400.

In some embodiments, the trained entity classification system 440 can be further refined. As various input NER spans are classified according to various detailed attributes by entity classification system 440, unsupervised learning techniques can be applied to suggest the creation of new detailed attributes or classifications into which the NER spans can be grouped. For example, the unsupervised learning techniques might dynamically suggest new detailed classifications when enough NER spans that are sufficiently different from the existing classification framework of entity classification system 440 have accumulated or been detected. In some embodiments, one or more continuous attributes can be added to the NER spans and classifications. For example, a Severity-tagged NER span can be associated with a continuous score indicating the severity of that specific span—in doing so, the potential error introduced by discrete bucketing or classification can be reduced or removed entirely.

As mentioned previously, entity classification system 440 can utilize one or more clinical lexicons, e.g., during training to perform first-pass annotations of input NER spans. Entity classification system 440 can additionally leverage these same clinical lexicons to extract or infer additional attributes and details about certain classifications that it may assign to input NER spans. When an NER span is linked to an existing entry in the clinical lexicon(s), significant semantic data can be deduced for that NER span—and this is often semantic data that would require millions of radiology report training data points in order for entity classification system 440 to learn the semantic information itself. For example, a span that reads "constriction near the branch of the iliac vein"—which poses the common classification complication in that a pathology is described but not identified by name—can be linked to an entry in the clinical lexicon for "iliac vein." On the basis of this linkage, the span can be labeled as identifying a lower-abdomen pathology. Although this does not necessarily identify the appropriate pathology indicated by the span, the 'lower-abdomen pathology' label does reduce the search space of possible candidate pathologies into which entity classification system 440 may ultimately classify the span. Notably, by linking NER spans to clinical lexicon entries, entity classification system 440 is able to extract and label the spans with anatomical information that otherwise could not be determined with NLP techniques alone.

In some embodiments, the semantic or anatomical information that entity classification system 440 extracts from the clinical lexicon(s) can additionally be used to infer relationships between terms. In the case of the example span discussed above, "constriction near the branch of the iliac vein," the anatomical information not only narrows the pathology to being a lower-abdomen pathology, but can be used to determine a linking relationship between the pathology and its location, either directly or as an additional input to entity relationship linking system 430. In some embodiments, entity classification system 440 can be located prior to (i.e., upstream of) entity relationship linking system 430, such that the aforementioned relationships extracted from NER spans on the basis of the clinical lexicon(s) can be provided as additional input to entity relationship linking system 430.

9. Implementation Example—Computer System

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques, or may include digital electronic devices such as at least one application-specific integrated circuit (ASIC) or field programmable gate array (FPGA) that is persistently programmed to perform the techniques, or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 6:
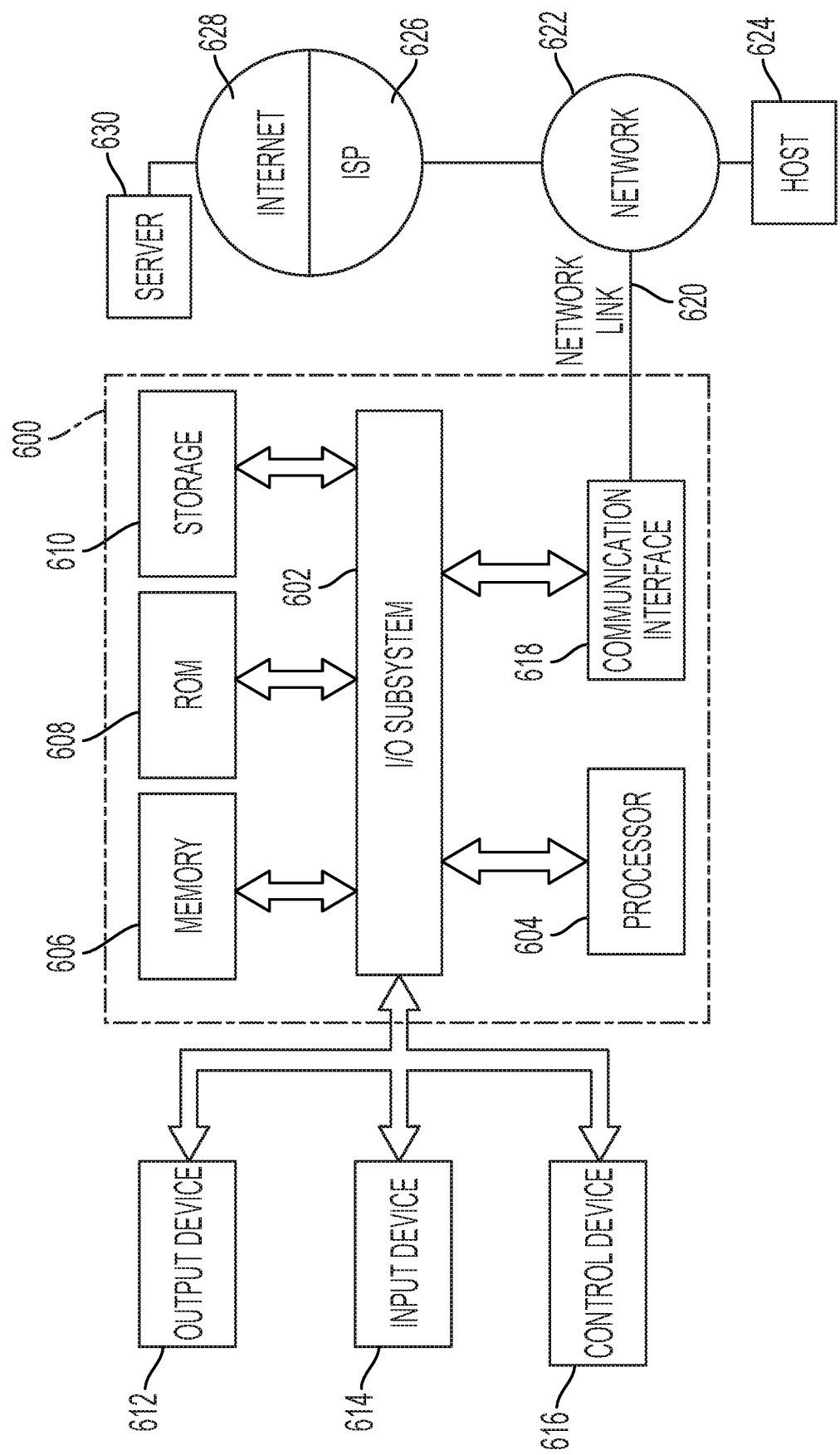
FIG. 6 illustrates an example computer system, with non-transitory computer-readable storage media, that may be used to implement all or part of one or more aspects of the present disclosure.

FIG. 6 is a block diagram that illustrates an example computer system with which an embodiment may be implemented. In the example of FIG. 6, a computer system 600 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 600 includes an input/output (I/O) subsystem 602 which may include a bus and/or other communication mechanism(s) for communicating information and/or instructions between the components of the computer system 600 over electronic signal paths. The I/O subsystem 602 may include an I/O controller, a memory controller and at least one I/O port. The electronic signal paths are represented schematically in the drawings, for example as lines, unidirectional arrows, or bidirectional arrows.

At least one hardware processor 604 is coupled to I/O subsystem 602 for processing information and instructions. Hardware processor 604 may include, for example, a general-purpose microprocessor or microcontroller and/or a special-purpose microprocessor such as an embedded system or a graphics processing unit (GPU) or a digital signal processor or ARM processor. Processor 604 may comprise an integrated arithmetic logic unit (ALU) or may be coupled to a separate ALU.

Computer system 600 includes one or more units of memory 606, such as a main memory, which is coupled to I/O subsystem 602 for electronically digitally storing data and instructions to be executed by processor 604. Memory 606 may include volatile memory such as various forms of random-access memory (RAM) or other dynamic storage device. Memory 606 also may be used for storing temporary variables or other intermediate information during execution of instructions to be executed by processor 604. Such instructions, when stored in non-transitory computer-readable storage media accessible to processor 604, can render computer system 600 into a special-purpose machine that is customized to perform the operations specified in the instructions.

Computer system 600 further includes non-volatile memory such as read only memory (ROM) 608 or other static storage device coupled to I/O subsystem 602 for storing information and instructions for processor 604. The ROM 608 may include various forms of programmable ROM (PROM) such as erasable PROM (EPROM) or electrically erasable PROM (EEPROM). A unit of persistent storage 610 may include various forms of non-volatile RAM (NVRAM), such as FLASH memory, or solid-state storage, magnetic disk or optical disk such as CD-ROM or DVD-ROM and may be coupled to I/O subsystem 602 for storing information and instructions. Storage 610 is an example of a non-transitory computer-readable medium that may be used to store instructions and data which when executed by the processor 604 cause performing computer-implemented methods to execute the techniques herein.

The instructions in memory 606, ROM 608 or storage 610 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 600 may be coupled via I/O subsystem 602 to at least one output device 612. In one embodiment, output device 612 is a digital computer display. Examples of a display that may be used in various embodiments include a touch screen display or a light-emitting diode (LED) display or a liquid crystal display (LCD) or an e-paper display. Computer system 600 may include other type(s) of output devices 612, alternatively or in addition to a display device. Examples of other output devices 612 include printers, ticket printers, plotters, projectors, sound cards or video cards, speakers, buzzers or piezoelectric devices or other audible devices, lamps or LED or LCD indicators, haptic devices, actuators or servos.

At least one input device 614 is coupled to I/O subsystem 602 for communicating signals, data, command selections or gestures to processor 604. Examples of input devices 614 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 616, which may perform cursor control or other automated control functions such as navigation in a graphical interface on a display screen, alternatively or in addition to input functions. Control device 616 may be a touchpad, a mouse, a trackball, or cursor direction keys for communicating direction information and command selections to processor 604 and for controlling cursor movement on display 612. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 614 may include a combination of multiple different input devices, such as a video camera and a depth sensor.

In another embodiment, computer system 600 may comprise an internet of things (IoT) device in which one or more of the output device 612, input device 614, and control device 616 are omitted. Or, in such an embodiment, the input device 614 may comprise one or more cameras, motion detectors, thermometers, microphones, seismic detectors, other sensors or detectors, measurement devices or encoders and the output device 612 may comprise a special-purpose display such as a single-line LED or LCD display, one or more indicators, a display panel, a meter, a valve, a solenoid, an actuator or a servo.

When computer system 600 is a mobile computing device, input device 614 may comprise a global positioning system (GPS) receiver coupled to a GPS module that is capable of triangulating to a plurality of GPS satellites, determining and generating geo-location or position data such as latitude-longitude values for a geophysical location of the computer system 600. Output device 612 may include hardware, software, firmware and interfaces for generating position reporting packets, notifications, pulse or heartbeat signals, or other recurring data transmissions that specify a position of the computer system 600, alone or in combination with other application-specific data, directed toward host 624 or server 630.

Computer system 600 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 600 in response to processor 604 executing at least one sequence of at least one instruction contained in main memory 606. Such instructions may be read into main memory 606 from another storage medium, such as storage 610. Execution of the sequences of instructions contained in main memory 606 causes processor 604 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 610. Volatile media includes dynamic memory, such as memory 606. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 602. Transmission media can also take the form of acoustic or light waves, such as those generated during radio-wave and infra-red data communications.

Various forms of media may be involved in carrying at least one sequence of at least one instruction to processor 604 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 600 can receive the data on the communication link and convert the data to a format that can be read by computer system 600. For instance, a receiver such as a radio frequency antenna or an infrared detector can receive the data carried in a wireless or optical signal and appropriate circuitry can provide the data to I/O subsystem 602 such as place the data on a bus. I/O subsystem 602 carries the data to memory 606, from which processor 604 retrieves and executes the instructions. The instructions received by memory 606 may optionally be stored on storage 610 either before or after execution by processor 604.

Computer system 600 also includes a communication interface 618 coupled to bus 602. Communication interface 618 provides a two-way data communication coupling to network link(s) 620 that are directly or indirectly connected to at least one communication networks, such as a network 622 or a public or private cloud on the Internet. For example, communication interface 618 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 622 broadly represents a local area network (LAN), wide-area network (WAN), campus network, internetwork or any combination thereof. Communication interface 618 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 618 sends and receives electrical, electromagnetic or optical signals over signal paths that carry digital data streams representing various types of information.

Network link 620 typically provides electrical, electromagnetic, or optical data communication directly or through at least one network to other data devices, using, for example, satellite, cellular, Wi-Fi, or BLUETOOTH technology. For example, network link 620 may provide a connection through a network 622 to a host computer 624.

Furthermore, network link 620 may provide a connection through network 622 or to other computing devices via internetworking devices and/or computers that are operated by an Internet Service Provider (ISP) 626. ISP 626 provides data communication services through a world-wide packet data communication network represented as internet 628. A server computer 630 may be coupled to internet 628. Server 630 broadly represents any computer, data center, virtual machine or virtual computing instance with or without a hypervisor, or computer executing a containerized program system such as DOCKER or KUBERNETES. Server 630 may represent an electronic digital service that is implemented using more than one computer or instance and that is accessed and used by transmitting web services requests, uniform resource locator (URL) strings with parameters in HTTP payloads, API calls, app services calls, or other service calls. Computer system 600 and server 630 may form elements of a distributed computing system that includes other computers, a processing cluster, server farm or other organization of computers that cooperate to perform tasks or execute applications or services. Server 630 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 630 may comprise a web application server that hosts a presentation layer, application layer and data storage layer such as a relational database system using structured query language (SQL) or no SQL, an object store, a graph database, a flat file system or other data storage.

Computer system 600 can send messages and receive data and instructions, including program code, through the network(s), network link 620 and communication interface 618. In the Internet example, a server 630 might transmit a requested code for an application program through Internet 628, ISP 626, local network 622 and communication interface 618. The received code may be executed by processor 604 as it is received, and/or stored in storage 610, or other non-volatile storage for later execution.

The execution of instructions as described in this section may implement a process in the form of an instance of a computer program that is being executed, and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 604. While each processor 604 or core of the processor executes a single task at a time, computer system 600 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

The term "cloud computing" is generally used herein to describe a computing model which enables on-demand access to a shared pool of computing resources, such as computer networks, servers, software applications, and services, and which allows for rapid provisioning and release of resources with minimal management effort or service provider interaction.

A cloud computing environment (sometimes referred to as a cloud environment, or a cloud) can be implemented in a variety of different ways to best suit different requirements. For example, in a public cloud environment, the underlying computing infrastructure is owned by an organization that makes its cloud services available to other organizations or to the general public. In contrast, a private cloud environment is generally intended solely for use by, or within, a single organization. A community cloud is intended to be shared by several organizations within a community; while a hybrid cloud comprises two or more types of cloud (e.g., private, community, or public) that are bound together by data and application portability.

Generally, a cloud computing model enables some of those responsibilities which previously may have been provided by an organization's own information technology department, to instead be delivered as service layers within a cloud environment, for use by consumers (either within or external to the organization, according to the cloud's public/private nature). Depending on the particular implementation, the precise definition of components or features provided by or within each cloud service layer can vary, but common examples include: Software as a Service (SaaS), in which consumers use software applications that are running upon a cloud infrastructure, while a SaaS provider manages or controls the underlying cloud infrastructure and applications. Platform as a Service (PaaS), in which consumers can use software programming languages and development tools supported by a PaaS provider to develop, deploy, and otherwise control their own applications, while the PaaS provider manages or controls other aspects of the cloud environment (i.e., everything below the run-time execution environment). Infrastructure as a Service (IaaS), in which consumers can deploy and run arbitrary software applications, and/or provision processing, storage, networks, and other fundamental computing resources, while an IaaS provider manages or controls the underlying physical cloud infrastructure (i.e., everything below the operating system layer). Database as a Service (DBaaS) in which consumers use a database server or Database Management System that is running upon a cloud infrastructure, while a DbaaS provider manages or controls the underlying cloud infrastructure, applications, and servers, including one or more database servers.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A natural language understanding method, the method comprising:
    obtaining a radiological report text, the radiological report text containing one or more clinical findings;
    in response to detecting one or more errors in the radiological report text, substituting a best replacement candidate for each of the one or more errors, the best replacement candidate calculated by analyzing a plurality of character-level optical transformation costs weighted by a frequency analysis over a corpus corresponding to the radiological report text;
    for each given word within the radiological report text:
        obtaining a word embedding;
        determining a plurality of character-level embeddings; and
        concatenating the word embedding and the plurality of character-level embeddings to a neural network;
    generating, using the neural network, a plurality of NER tagged spans for the radiological report text, the generating based on the concatenated word and character-level embedding s;
    calculating a set of linked relationships for the plurality of NER tagged spans by:
        generating one or more masked text sequences based on the radiological report text and determined pairs of potentially linked NER spans;
        calculating a dense adjacency matrix based on attention weights obtained from providing the one or more masked text sequences to a Transformer deep learning network; and
        performing graph convolutions over the calculated dense adjacency matrix via a graph convolutional network.

2. The method of claim 1, wherein using the neural network to generate the plurality of NER tagged spans comprises:

classifying each given word within the radiological report text by applying an IOB (Inside-Outside-Beginning) tagging scheme;

generating a plurality of spans from words having a Beginning tag or an Inside tag; and generating the plurality of NER tagged spans by classifying each one of the plurality of spans over a pre-defined set of classes.

3. The method of claim 2, wherein the pre-defined set of classes comprises a Pathology class, a Severity class, and a Location class.

4. The method of claim 3, further comprising:

training a classifier over a pre-defined lexicon of clinical terminology; and providing the plurality of NER tagged spans to the trained classifier, such that the trained classifier labels NER tagged spans of the Pathology class with a specific pathology type.

5. The method of claim 4, further comprising providing the plurality of NER tagged spans to the trained classifier such that the trained classifier:

labels NER tagged spans of the Severity class with a severity level; and labels NER tagged spans of the Location class with a specific anatomical location.

6. The method of claim 5, wherein:

the severity level is a continuous numerical score value; and the anatomical location is a specific motion segment.

7. The method of claim 4, wherein the pre-defined lexicon of clinical terminology comprises a pre-trained model of biomedical word embeddings or Word2vec encodings.

8. The method of claim 4, wherein training the classifier over a pre-defined lexicon of clinical terminology further comprises refining the classifier by generating augmented training data, the augmented training data generated in response to analyzing a first pass classification performed using the pre-defined lexicon of clinical terminology.

9. The method of claim 8, further comprising iteratively generating augmented training data based on an analysis of a prior training round to detect words having a low frequency of occurrence and a high feature weight in a classification model of the classifier.

10. The method of claim 2, wherein the neural network used to generate the plurality of NER tagged spans is an ordered-neuron Long short-term memory (ON-LSTM) using a conditional random field (CRF) to classifying the plurality of spans over the pre-defined set of classes.

11. The method of claim 1, wherein obtaining the radiological report text comprises providing an image of a radiological report to one or more optical character recognition (OCR) engines, the radiological report text generated from the outputs of the one or more OCR engines.

12. The method of claim 1, wherein the plurality of character-level optical transformation costs is used to calculate weighted Levenshtein distances between a detected error word in the radiological report text and a plurality of potential replacement candidate words.

13. The method of claim 1, wherein the corpus corresponding to the radiological report text is a corpus of terms specific to a determined type of radiological exam represented in the radiological report text.

14. The method of claim 1, further comprising, in response to detecting one or more errors in the radiological report text:

generating a plurality of potential replacement candidates based on the analysis of the character-level optical transformation costs and the frequency analysis;

obtaining embeddings for one or more words adjacent to the detected error in the radiological report text;

analyzing each potential replacement candidate against the embeddings of the one or more adjacent words, using a masked language model; and calculating the best replacement candidate based on the highest probability output from the masked language model analysis.

15. The method of claim 14, wherein the masked language model is Clinical BERT-based (Bidirectional Encoder Representations from Transformers) machine learning network.

16. The method of claim 14, further comprising using the masked language model to calculate a clinical significance of mistake for each potential replacement candidate by analyzing each potential replacement candidate against the embeddings of the one or more adjacent words.

17. The method of claim 1, wherein generating the one or more masked text sequences comprises, for each given pair of potentially linked NER tagged spans:

obtaining, from the radiological report text, a sentence portion containing both NER tagged spans of the given pair;

masking both NER tagged spans with an identifier, the identifier corresponding to a class of the NER tagged span; and generating a masked text sequence for the given pair by replacing the NER tagged spans in the sentence portion with the identifiers.

18. The method of claim 1, wherein generating the one or more masked text sequences comprises generating a single masked text sequence for the plurality of potentially linked NER tagged spans by:

masking each NER tagged span of the plurality of potentially linked NER tagged spans with an identifier, the identifier corresponding to a class of the NER tagged span; and generating the single masked text sequence by replacing each NER tagged span in the radiological report text with its corresponding identifier.

19. The method of claim 18, further comprising providing the single masked text sequence to a BERT-AL (BERT for Arbitrarily Long Document Understanding) machine learning network.

20. The method of claim 1, further comprising calculating the set of linked relationships for the plurality of NER tagged spans by providing to a dense classifier the output of the graph convolutions over the calculated dense adjacency matrix, and one or more head masks and tail masks calculated for the masked text sequences provided to the Transformed deep learning network.

* * * * *